United States Patent [19]

Kawai et al.

[11] Patent Number: 5,530,119
[45] Date of Patent: Jun. 25, 1996

[54] SUBSTITUTED ALICYCLIC AMINE-CONTAINING MACROCYCLIC IMMUNOMODULATORS

[75] Inventors: Megumi Kawai; Jay R. Luly, both of Libertyville, Ill.

[73] Assignee: Abbott Laboratories, Abbott Park, Ill.

[21] Appl. No.: 341,255

[22] Filed: Nov. 17, 1994

Related U.S. Application Data

[63] Continuation of Ser. No. 99,975, Jul. 30, 1993, abandoned, which is a continuation-in-part of Ser. No. 32,958, Mar. 17, 1993, abandoned.

[51] Int. Cl.$^6$ .......................... C07D 498/12; A61K 31/33
[52] U.S. Cl. .............................................................. 540/456
[58] Field of Search ............................................. 540/456

[56] References Cited

U.S. PATENT DOCUMENTS

| | | | |
|---|---|---|---|
| 4,894,366 | 1/1990 | Okuhara et al. | 540/456 |
| 5,208,228 | 5/1993 | Ok et al. | 540/456 |
| 5,208,241 | 5/1993 | Ok et al. | 540/456 |
| 5,262,533 | 11/1993 | Sinclair et al. | 540/456 |

FOREIGN PATENT DOCUMENTS

| | | | |
|---|---|---|---|
| 428365 | 5/1991 | European Pat. Off. | 540/456 |
| WO92/20688 | 11/1992 | WIPO | 540/456 |

*Primary Examiner*—Robert T. Bond
*Attorney, Agent, or Firm*—Steven R. Crowley; Gregory W. Steele

[57] ABSTRACT

Compounds having the formula

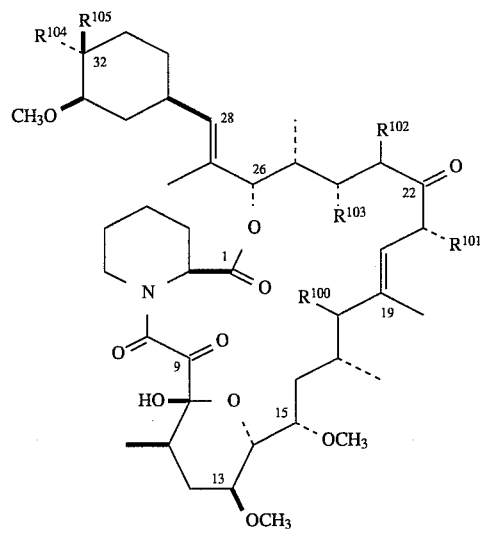

and pharmaceutically acceptable salts, esters, amides and prodrugs thereof, wherein one of $R^{104}$ and $R^{105}$ is hydrogen, and the other of $R^{104}$ and $R^{105}$ is a group having the formula

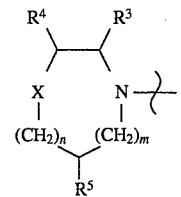

as well as pharmaceutically compositions containing such compounds and methods of immunomodulative therapy utilizing the same.

16 Claims, No Drawings

SUBSTITUTED ALICYCLIC AMINE-CONTAINING MACROCYCLIC IMMUNOMODULATORS

This application is a continuation of U.S. patent application Ser. No. 08/099,975, filed Jul. 30, 1993, now abandoned, which is a continuation-in-part of the U.S. patent application Ser. No. 08/032,958, filed on Mar. 17, 1993, now abandoned.

FIELD OF THE INVENTION

The present invention relates to novel chemical compounds having immunomodulatory activity, and in particular to macrolide immunosuppressants. More particularly, the invention relates to semisynthetic analogs of ascomycin and FK-506, means for their preparation, pharmaceutical compositions containing such compounds and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Unsatisfactory side-effects associated with cyclosporine, however, such as nephrotoxicity, have led to a continued search for immunosuppressant compounds having improved efficacy and safety.

Recently, several classes of macrocyclic compounds having potent immunomodulatory activity have been discovered. Okuhara et al., in European Patent Application No. 184162, published Jun. 11, 1986, disclose a number of macrocyclic compounds isolated from the genus Streptomyces. Immunosuppressant FK-506, isolated from a strain of $S.$ $tsukubaensis$, is a 23-membered macrocyclic lactone represented by formula 1a, below. Other related natural products, such as FR-900520 (1b) and FR-900523 (1c), which differ from FK-506 in their alkyl substituent at C-21, have been isolated from $S.$ $hygroscopicus$ $yakushimnaensis.$ Yet another analog, FR-900525, produced by $S.$ $tsukubaensis,$ differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monaghan, R. L., et al., on the other hand, describe the use of ascomycin as an immunosuppressant in European Patent Application No. 323865, published Jul. 12, 1989.

Although the immunosuppressive activity of FK-506 has been clinically confirmed, toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

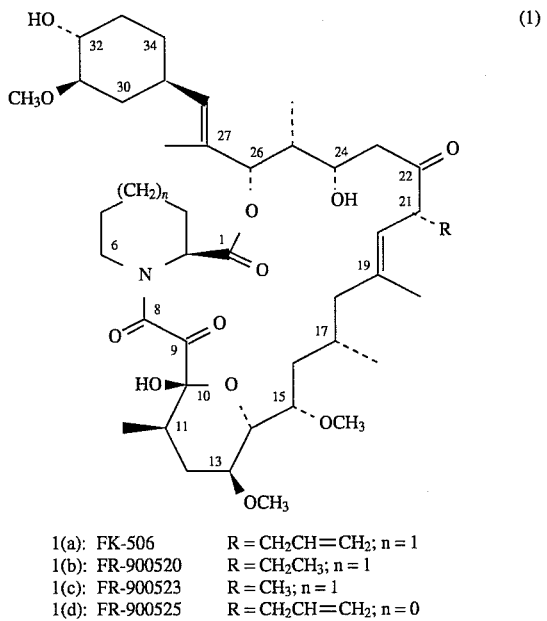

| | | |
|---|---|---|
| 1(a): | FK-506 | $R = CH_2CH=CH_2$; n = 1 |
| 1(b): | FR-900520 | $R = CH_2CH_3$; n = 1 |
| 1(c): | FR-900523 | $R = CH_3$; n = 1 |
| 1(d): | FR-900525 | $R = CH_2CH=CH_2$; n = 0 |

Fermentation products of FK-type compounds include C-21-epi derivatives of FK-506; a 31-demethylated derivative of FK-506; 31-oxo-FK-506; and compounds derived from FK-506, FR-900523 and FR-900525 which are characterized by the introduction of hydroxy-protecting groups, formation of a double bond by elimination of water between carbons 23 and 24, oxidation of the hydroxy group at carbon 24 to the ketone, and reduction of the allyl side-chain at carbon 21 via hydrogenation. Other published derivatives include those derived from FK-506 and FR-900520 where the lactone ring is contracted to give a macrocyclic ring containing two fewer carbons.

Several microbial transformations of FK-type compounds at carbon 13 have been published, such as the microbial demethylation of FR-900520 to form the bis-demethylated 13,31-dihydroxy ring-rearranged derivative of FR-900520; the microbial monodemethylation of FK-506 and FR-900520, respectively; and the microbial demethylation of FR-900520 at C-31, as well as a number of other macrocyclic microbial transformation products.

Numerous chemical modifications of the FK-type compounds have been attempted. These include the preparation of small synthetic fragments of FK-type derivatives; a thermal rearrangement of a variety of derivatives of FK-506 which expands the macrocyclic ring by two carbons; and modifications which include methyl ether formation at C-32 and/or C-24, oxidation of C-32 alcohol to the ketone, and epoxide formation at C-9.

Although some of these modified compounds exhibit immunosuppressive activity, the need remains for macrocyclic immunosuppressants which do not have the serious side effects frequently associated with immunosuppressant therapy. Accordingly, one object of the invention is to provide novel semisynthetic macrolides which possess the desired immunomodulatory activity but which may be found to minimize untoward side effects.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient, one of the above compounds. Yet another object of the invention is to provide a method of treating a variety of disease states, including post-transplant tissue rejection and autoimmune disfunction.

SUMMARY OF THE INVENTION

In one aspect of the present invention are disclosed compounds having the formula

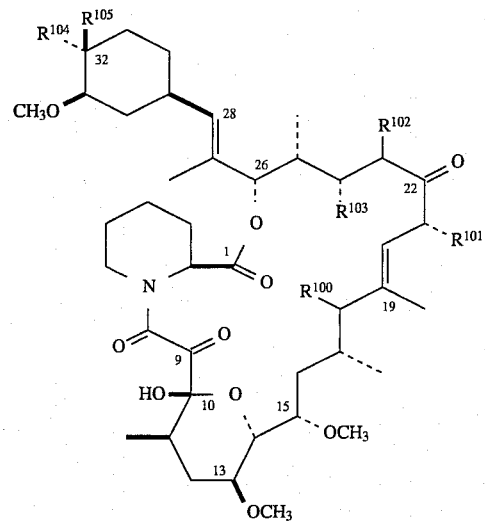

and the pharmaceutically acceptable salts, esters, amides and prodrugs thereof, wherein $R^{100}$ is hydrogen, hydroxy, halogen, —$OR^{13}$ or —$OR^{14}$;

$R^{101}$ is methyl, ethyl, allyl or propyl;

$R^{102}$ is hydrogen and $R^{103}$ is selected from (a) hydrogen, (b) hydroxyl and (c) hydroxyl protected by a hydroxy-protecting group or, taken together, $R^{102}$ and $R^{103}$ form a bond; and one of $R^{104}$ and $R^{105}$ is hydrogen, and the other of $R^{104}$ and $R^{105}$ is a group having the formula

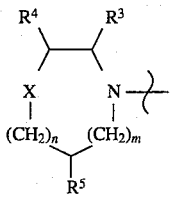

where m and n are independently zero, one or two;

X is selected from the group consisting of oxygen, —$S(O)_s$— where s is zero, one or two, —$N(R^1)$— and —$C(R^{2})(R^{2'})$—, or is absent; and $R^3$, $R^4$ and $R^5$ are independently selected from the group consisting of (a) hydrogen; (b) alkyl; (c) haloalkyl; (d) cycloalkyl; (e) cycloalkylalkyl; (f) alkenyl; (g) alkynyl; (h) hydroxyalkyl; (i) hydroxylalkoxyalkyl; (j) aryl substituted by $R^6$, $R^7$ and $R^8$; (j') arylalkyl substituted by $R^6$, $R^7$ and $R^8$; (k) alkoxycarbonyl; (l) alkoxycarbonylalkyl; (m) carboxyalkyl; (n) aminoalkyl; (o) thiolalkyl; (q) heterocyclic; (r) (heterocyclic)alkyl; (s) (heterocyclic)alkylaminoalkyl; (p) acyl; (u) N-mono- or N,N-dialkylaminoalkyl; (v) N-mono- or N,N-dialkylcarboxamidoalkyl; (w) N-mono- or N,N-diarylcarboxamidoalkyl; (x) formyl; (x') protected formyl; (z) (heterocyclic)alkenyl; and (aa) (heterocyclic)alkynyl. Alternatively, $R^3$ and $R^5$, when taken together, may form a methylene —$CH_2$— so that the group of Formula (11) becomes a bicyclic radical.

In the above, $R^1$ is selected from the group consisting of (a) hydrogen; (b) alkyl; (c) haloalkyl; (d) cycloalkyl; (e) cycloalkylalkyl; (f) alkenyl; (g) alkynyl; (h) hydroxyalkyl; (i) hydroxylalkoxyalkyl; (j) aryl substituted by $R^6$, $R^7$ and $R^8$; (j') arylalkyl substituted by $R^6$, $R^7$ and $R^8$; (k) alkoxycarbonyl; (l) alkoxycarbonylalkyl; (m)carboxyalkyl; (n) aminoalkyl; (o) thiolalkyl; (p) —$S(O)_x$—$R^9$, wherein x is one or two and $R^9$ is selected from the group consisting of alkyl, aryl, and arylalkyl; (q) heterocyclic; (r) (heterocyclic)alkyl; (s) (heterocyclic)alkylaminoalkyl; (t) acyl; (u) N-mono- or N,N-dialkylaminoalkyl; (v) N-mono- or N,N-dialkylcarboxamidoalkyl; (w) N-mono- or N,N-diarylcarboxamidoalkyl; (x) formyl; (x') protected formyl; (y) —$P(O)(OR^{10})(OR^{10'})$ where $R^{10}$ and $R^{10'}$ are independently selected from the group consisting of loweralkyl, arylalkyl and aryl; (z) (heterocyclic)alkenyl; (aa) (heterocyclic)-alkynyl; (bb) urea; (cc) nitro; and (dd) polyhydroxylalkyl.

$R^2$ and $R^{2'}$ in the above are independently selected from the group consisting of hydrogen, hydroxy, hydroxyalkyl, amidoalkyl, N-alkylcarboxamido, N,N-dialkylamino, pyrrolidin-1-yl and piperidin-1-yl, or, taken together, $R^2$ and $R^{2'}$ are oxo, thiooxo or —$O(CH_2)_iO$—, where i is two, three or four.

$R^6$, $R^7$ and $R^8$ in the above are independently selected from (i) hydrogen; (ii) —($C_1$-to-$C_7$ alkyl); (iii) —($C_2$-to-$C_6$ alkenyl); (iv) halogen; (v) —$(CH_2)_mNR^{11}R^{11'}$ where m is an integer between one and ten, inclusive, and $R^{11}$ and $R^{11'}$ are independently selected from the group consisting of hydrogen, alkyl, aryl, arylalkyl, heterocyclic, (heterocyclic)alkyl, (heterocyclic)alkenyl and (heterocyclic)alkynyl; (vi) —CN; (vii) —CHO; (viii) mono-, di-, tri- or perhalogenated alkyl; (ix) —$S(O)_sR^{11}$ where s is zero, one or two; (x) —$C(O)NR^{11}R^{11'}$; (xi) —$(CH_2)_mOR^{11}$; (xii) —$CH(OR^{12})(OR^{12'})$, where $R^{12}$ and $R^{12'}$ are independently —($C_1$-to-$C_3$ alkyl) or, taken together, form an ethylene or propylene bridge; (xiii) —$(CH_2)_mOC(O)R^{11}$; (xiv) —$(CH_2)_mC(O)OR^{11}$; (xv) —$OR^{13}$; (xvi) —$S(O)_tNR^{11}R^{11'}$, where t is one or two; (xvii) —$NO_2$; (xviii) —$N_3$; and (xviv) guanidino optionally substituted by a radical selected from the group consisting of loweralkyl, aryl, acyl, arylsulfonyl, alkoxycarbonyl, arylalkoxycarbonyl, aryloxycarbonyl and alkylsulfonyl. Alternatively, any two adjacent $R^6$, $R^7$ and $R^8$ and the atoms to which they are attached may form a carbocyclic or heterocyclic ring having 5, 6 or 7 ring atoms which optionally include one or two additional heteroatoms independently selected from the group consisting of —O—, —$S(O)_s$— where s is zero, one or two, and —$NR^{11}$—.

$R^{13}$ in the above is selected from (i) —$PO(OH)O^-M^+$, (ii) —$SO_3^-M^+$, and (iii) —$C(O)(CH_2)_mC(O)O^-M^+$, where $M^+$ is a proton or a positively charged inorganic or organic counterion, and m is an integer between one and ten, inclusive.

$R^{14}$ in the above is selected from the group consisting of (i) acyl; (ii) —($C_1$-to-$C_7$ alkyl); (iii) —($C_2$-to-$C_6$ alkenyl); (vi) —$(CH_2)_mNR^{11'}$, where m is an integer between one and ten, inclusive; (v) —$S(O)_sR^{11}$, where s is zero, one or two; (vi) —$C(O)NR^{11}R^{11'}$; (vii) —$(CH_2)_mOR^{11}$; (viii) —$CH(OR^{12})(OR^{12'})$; (ix) —$(CH_2)_mOC(O)R^{11}$; (x) —$(CH_2)_mC(O)OR^{11}$; and (xi) —$S(O)_tNR^{11}R^{11'}$, where t is one or two;

In another aspect of the present invention are disclosed pharmaceutical compositions, comprising a compound of the invention in combination with a pharmaceutically acceptable carrier.

In a further aspect of the present invention is disclosed a method for treating a patient in need of immunomodulative therapy, comprising administering to such a patient a therapeutically effective amount of a compound of the invention for such time as is necessary to obtain the desired therapeutic effect.

DETAILED DESCRIPTION OF THE INVENTION

Among the preferred compounds of the present invention are those having formula (I) in which:

m and n are independently zero or one;

X is selected from the group consisting of —S(O)$_s$— and —N(R$^1$)—; and/or

R$^1$, R$^3$, R$^4$ and R$^5$ are independently selected from the group consisting of (a) hydrogen; (b) alkyl; (c) cycloalkyl; (d) cycloalkylalkyl; (e) hydroxyalkyl; (f) hydroxylalkoxyalkyl; (g) aryl substituted by R$^6$, R$^7$ and R$^8$; (h) arylalkyl substituted by R$^6$, R$^7$ and R$^8$; (i) alkoxycarbonyl; (j) alkoxycarbonylalkyl; (k) carboxyalkyl; (l) aminoalkyl; (m) thiolalkyl; (n) heterocyclic; (o) (heterocyclic)alkyl; (p) (heterocyclic)alkylaminoalkyl; (q) acyl; (r) N-mono- or N,N-dialkylaminoalkyl; (s) N-mono- or N,N-dialkylcarboxamidoalkyl; (t) N-mono- or N,N-diarylcarboxamidoalkyl; and (u) formyl.

Also preferred are those compounds in which X in the heterocyclic ring of formula (II) is selected from the group consisting of —N(R$^1$)— and —C(R$^2$)(R$^{2'}$)—, and the total of m and n is zero, one or two (that is, where the heterocycle is a 5- to 7-membered ring).

Representative of the compounds of the present invention are those which are demonstrated in Examples 5, 7, 9, 11–22, 27, 28, 31, 38, 39, 44, 58, 61, 62, 67, 76 and 105–111, below. The most preferred of these compounds, and that contemplated as the best mode thereof, is the compound described in Example 17 hereof.

As used throughout this specification and in the appended claims, the following terms have the meanings specified:

The term "acyl" as used herein refers to an aryl or alkyl group, as defined below, appended to a carbonyl group including, but not limited to, acetyl, pivaloyl, benzoyl and the like.

The term "alkenyl" as used herein refers to straight or branched chain groups of 2 to 12 carbon atoms containing a carbon-carbon double bond including, but not limited to ethenyl, 1-propenyl, 2-propenyl, 2-methyl-1-propenyl, 1-butenyl, 2-butenyl and the like.

The terms "alkoxy" as used herein refer to a loweralkyl group, as defined below, attached to the remainder of the molecule through an oxygen atom including, but not limited to, methoxy, ethoxy, isopropoxy, n-butoxy, sec-butoxy, isobutoxy, tert-butoxy and the like.

The terms "alkoxyalkyl" as used herein refers to an alkoxy group, as defined above, appended to an alkyl group including, but not limited to, methoxymethyl, ethoxymethyl, methoxyethyl, ethoxyethyl, i-propyloxymethyl, n-butoxyethyl and the like.

The term "alkoxycarbonyl" as used herein refers to an alkoxy group, as defined above, attached via a carbonyl group including, but not limited to, methyloxycarbonyl, ethyloxycarbonyl, tert-butyloxycarbonyl, cyclohexyloxycarbonyl and the like.

The term "alkoxycarbonylalkyl" as used herein refers to an alkoxycarbonyl group, as defined above, attached via an alkyl group including, but not limited to, methyloxycarbonylmethyl, ethyloxycarbonylethyl, tert-butyloxycarbonylmethyl, cyclohexyloxycarbonylmethyl and the like.

The term "alkyl" as used herein refers to a monovalent straight chain or branched chain group of 1 to 12 carbon atoms including, but not limited to, methyl, ethyl, n-propyl, isopropyl, n-butyl, sec-butyl, isobutyl, tert-butyl and the like.

The terms "alkylamino" and "loweralkylamino" as used herein refer to a group having the structure —NH—(loweralkyl), where the loweralkyl portion is as defined below. Alkylamino and loweralkylamino groups include, for example, methylamino, ethylamino, isopropylamino and the like.

The term "alkylsulfonyl" as used herein refers to an alkyl group, as defined above, attached via a sulfur dioxide diradical including, but not limited to, methanesulfonyl, camphorsulfonyl and the like.

The terms "alkylthioether", "thioalkoxy" and "thioloweralkoxy" as used herein refer to a loweralkyl group, as previously defined, attached via a sulfur atom including, but not limited to, thiomethoxy, thioethoxy, thioisopropoxy, n-thiobutoxy, sec-thiobutoxy, isothiobutoxy, tert-thiobutoxy and the like.

The term "alkynyl" as used herein refers to straight or branched chain groups of 2 to 12 carbon atoms containing a carbon-carbon triple bond including, but not limited to acetylenyl, propargyl and the like.

The term "amidoalkyl" as used herein refers to a group having the structure —N(R$^{401}$)C(O)R$^{402}$ appended to a loweralkyl group, as previously defined. The groups R$^{401}$ and R$^{402}$ are independently selected from hydrogen, lower alkyl, aryl, arylalkyl, and halosubstituted alkyl. Alternatively, R$^{401}$ and R$^{402}$, taken together, may be —(CH$_2$)$_{aa}$— where aa is an integer of from two to six.

The term "aminoalkyl" as used herein refers to a group having the structure —NR$_{403}$R$_{404}$ appended to a loweralkyl group, as previously defined. The groups R$_{403}$ and R$_{404}$ are independently selected from hydrogen, lower alkyl, aryl and arylalkyl. Alternatively, R$_{403}$ and R$_{404}$, taken together, may be —(CH$_2$)$_{bb}$— where bb is an integer of from two to six.

The terms "aryl" as used herein refers to carbocyclic aromatic groups including, but not limited to, phenyl, 1- or 2-naphthyl, fluorenyl, (1, 2)-dihydronaphthyl, (1,2,3,4)-tetrahydronaphthyl, indenyl, indanyl and the like.

The terms "arylalkoxy" and "arylalkylether" as used herein refer to an arylalkyl group, as defined below, attached to the parent molecular moiety through an oxygen atom. Arylalkoxy includes, but is not limited to, benzyloxy, 2-phenethyloxy, 1-naphthylmethyloxy and the like.

The term "arylalkoxycarbonyl" as used herein refers to an arylalkoxy group, as defined above, attached via a carbonyl group including, but not limited to, benzyloxycarbonyl, 9-fluorenylmethyloxycarbonyl and the like.

The term "arylalkyl" as used herein refers to an aryl group, as previously defined, appended to an alkyl group including, but not limited to, benzyl, 1- and 2-naphthylmethyl, halobenzyl, alkoxybenzyl, hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The terms "arylether" and "aryloxy" as used herein refer to an aryl group, as previously defined, attached to the parent molecular moiety through an oxygen atom. Aryloxy and arylether include, but are not limited to, phenoxy, 1-naphthoxy, 2-naphthoxy and the like.

The term "aryloxycarbonyl" as used herein refers to an aryloxy group, as defined above, attached via a carbonyl group including, but not limited to, phenyloxycarbonyl, The term "aryloxycarbonylamino" as used herein refers to an aryloxycarbonyl group, as defined above, appended to an amino group including, but not limited to, phenyloxycarbonylamino.

The term "arylsulfonyl" as used herein refers to an aryl group, as defined above, attached via a sulfur dioxide diradical including, but not limited to p-toluenesulfonyl, benzenesulfonyl and the like.

The terms "arylthioether" and "thioaryloxy" as used herein refer to an aryl group, as defined above, attached via a sulfur atom.

The term "carboxamido" as used herein refers to an amino group attached via a carbonyl group and having the formula —C(O)NH$_2$.

The term "carboxyalkyl" as used herein refers to a carboxyl group, —CO$_2$H, appended to a loweralkyl group, as previously defined.

The term "cycloalkenyl" as used herein refers to a cyclic group of 5 to 10 carbon atoms possessing one or more carbon-carbon double bonds including, but not limited to, cyclopentenyl, cyclohexenyl and the like, in which the point of attachment can occur at any available valency on the carbocylic ring.

The term "cycloalkyl" as used herein refers to a cyclic group of 3 to 8 carbon atoms including, but not limited to, cyclopropyl, cyclobutyl, cyclopentyl, cyclohexyl and the like.

The term "cycloalkylalkenyl" as used herein refers to a cycloalkyl group, as defined above, appended to an alkenyl group, as defined above.

The term "cycloalkylalkyl" as used herein refers to a cycloalkyl group appended to a lower alkyl group including, but not limited to, cyclohexylmethyl and cyclohexylethyl.

The term "cycloalkylalkynyl" as used herein refers to cycloalkyl, as defined above, appended to an alkynyl group, as defined above.

The term "guanidinoalkyl" as used herein refers to a group of the structure —N(R$^{405}$)C(=NR$^{406}$)NHR$^{407}$ appended to a loweralkyl group, as previously defined. R$^{405}$, R$^{406}$ and R$^{407}$ are independently selected from hydrogen, lower alkyl, heterocyclic, aminoalkyl and aryl. Alternatively, R$^{406}$ and R$^{407}$, taken together, may be —(CH$_2$)$_{cc}$— where cc is an integer of from two to six.

The terms "halo" and "halogen" as used herein refer to an atom selected from fluorine, chlorine, bromine and iodine.

The terms "haloalkyl" as used herein refer to halogen appended to an alkyl group, as previously defined.

The term "heterocyclic" as used herein, except where otherwise specified, refers to any aromatic or non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 3 double bonds, (ii) the nitrogen and sulfur heteroatoms as well as the carbon atoms may optionally be oxidized by unsaturation and/or substitution by hydroxy, thiol, oxo or thiooxo, (iii) the nitrogen heteroatom may optionally be quarternized, (iv) any of the above heterocyclic rings may be fused to a benzene ring. Representative heterocycles include, but are not limited to, pyrrolyl, pyrrolidinyl, pyrazolyl, pyrazolinyl, pyrazolidinyl, cytosinyl, thiocytosinyl, imidazolyl, imidazolinyl, imidazolidinyl, pyridyl, piperidinyl, pyrazinyl, piperazinyl, pyrimidinyl, pyridazinyl, xanthenyl, xanthonyl, xanthopterinyl, oxazoyl, oxazolidinyl, thiouracilyl, isoxazolyl, isoxazolidinyl, morpholinyl, indolyl, quinolinyl, uracilyl, urazolyl, uricyl, thiazolyl, thiazolidinyl, isothiazolyl, isothiazolidinyl, isoquinolinyl, thyminyl, benzimidazolyl, benzothiazolyl, benzoxazolyl, furyl, thienyl and benzothienyl.

The term "(heterocyclic)alkyl" as used herein refers to a heterocyclic group appended to an alkyl group, as previously defined.

The term "(heterocyclic)alkylaminoalkyl" as used herein refers to a (heterocyclic)alkyl group appended to an aminoalkyl group, as previously defined.

The term "(heterocyclic)alkylether" as used herein refers to a (heterocyclic)alkyl moiety, as defined above, attached via an oxygen atom.

The term "(heterocyclic)alkenyl" as used herein refers to a heterocyclic group appended to an alkenyl group, as previously defined.

The term "(heterocyclic)alkylthioether" as used herein refers to a (heterocyclic)alkyl moiety, as defined above, attached via a sulfur atom.

The term "(heterocyclic)alkynyl" as used herein refers to a heterocyclic group appended to an alkynyl group, as previously defined.

The term "(heterocyclic)ether" as used herein refers to a heterocyclic moiety, as defined above, attached via an oxygen atom.

The term "(heterocyclic)thioether" as used herein refers to a heterocyclic moiety, as defined above, attached via a sulfur atom.

The terms "hydroxyalkyl" as used herein refer to —OH appended to a loweralkyl group, as defined below.

The terms "hydroxyalkyloxyalkyl" as used herein refer to —OH appended to an alkyloxyalkyl group, as defined above.

The term "hydroxy-protecting group" as used herein refers to those groups which are known in the art to protect a hydroxyl group against undesirable reaction during synthetic procedures and to be selectively removable including, but not limited to, dimethylthexylsilyl, trisubstituted silyl such as tri(lower)alkylsilyl (e.g. trimethylsilyl, triethylsilyl, tributylsilyl, tri-i-propylsilyl, tert-butyl-dimethylsilyl, tri-tert-butylsilyl, triphenylmethyl-dimethylsilyl, etc.); lower alkyldiarylsilyl (e.g. methyl-diphenylsilyl, ethyl-diphenylsilyl, propyl-diphenylsilyl, tert-butyl-diphenylsilyl, etc.), and the like; triarysilyl (e.g. triphenylsilyl, tri-p-xylylsilyl, etc.); triarylalkylsilyl (e.g. tribenzylsilyl, etc.), acyl substituted with an aromatic group and the like. Other classes of hydroxy-protecting group which may be useful include, but are not limited to, chlorocarbonate analogues such as trimethylsilylethoxycarbonyl, methylthiomethoxyethoxycarbonyl or benzenesulfonylethoxycarbonyl; trimethylsilylethoxymethyl, and the like, The term "loweralkyl" as used herein refers to an alkyl group, as defined above, of 1 to 8 carbon atoms.

The terms "monoalkylamino" and "dialkylamino" refer respectively to one and two alkyl or cycloalkyl groups, as defined above, appended to an amino group including, but not limited to, methylamino, isopropylamino, cyclohexylamino, dimethylamino, N,N-methylisopropylamino; bis-(cyclohexyl)amino and the like.

The term "N-alkylcarboxamido" as used herein refers to an alkylamino group, as defined above, attached via a carbonyl group and having the formula HN(alkyl)C(O)—.

The term "N-arylcarboximido" as used herein refers to an arylamino group, as defined above, attached via a carbonyl group and having the formula HN(aryl)C(O)—.

The term "N,N-dialkylcarboxamido" as used herein refers to an amino group substituted with two alkyl groups, as defined above, wherein the two alkyl groups need not be identical, attached via a carbonyl group and having the formula N(alkyl)(alkyl')C(O)—.

The term "N,N-diarylcarboxamido" as used herein refers to an amino group substituted with two aryl groups, as defined above, wherein the two aryl groups need not be identical, attached via a carbonyl group and having the formula N(aryl)(aryl')C(O)—.

The term "N-alkylcarboxamidoalkyl" as used herein refers to an alkylcarboxamido group, as defined above, attached via an alkyl group and having the formula HN(alkyl)C(O)—alkyl—.

The term "N-arylcarboxamidoalkyl" as used herein refers to an arylcarboxamido group, as defined above, attached via an alkyl group and having the formula HN(aryl)C(O)—alkyl—.

The term "N,N-dialkylcarboxamidoalkyl" as used herein refers to an amino group substituted with two alkyl groups, as defined above, wherein the two alkyl groups need not be identical, attached via a carbonyl group and having the formula N(alkyl)(alkyl')C(O)—alkyl—.

The term "N,N-diarylcarboxamido" as used herein refers to an amino group substituted with two aryl groups, as defined above, wherein the two aryl groups need not be identical, attached via a carbonyl group and having the formula N(aryl)(aryl')C(O)—alkyl—.

The term "oxo" as used herein refers to an oxygen atom forming a carbonyl group.

The term "polyhydroxyalkyl" as used herein refers to two or more hydroxyl groups appended to an alkyl group, as defined above.

The term "protected formyl group" as used herein refers to those groups which are known in the art to protect a formyl group against undesirable reaction during synthetic procedures and to be selectively removable including, but not limited to, dimethyl acetal, diethyl acetal, bis(2,2,2-trichloroethyl) acetals, Dibenzyl acetal, 1,3-dioxane, 5-methylene-1,3-dioxane, 5,5-dibromo-1,3-dioxane, O-methyl-S-2-(methylthio)ethyl acetal, 1,3-oxathiolanes and the like.

The term "thioalkoxyalkyl" as used herein refers to a thioalkoxy group, as defined above, appended to a lower-alkyl group.

The term "thioalkyl" as used herein refers to an alkyl group, as defined above, attached via a sulfur atom.

The term "thiooxo" as used herein refers to a sulfur atom forming a thiocarbonyl group.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge, et al., "Pharmaceutical Salts," *J. Pharm. Sci.*, 66: 1–19 (1977) which is incorporated herein by reference.)

Examples of pharmaceutically acceptable, non-toxic esters of the compounds of this invention include $C_1$-to-$C_6$ alkyl esters wherein the alkyl group is a straight or branched chain. Acceptable esters also include $C_5$-to-$C_7$ cycloalkyl esters as well as arylalkyl esters such as, but not limited to benzyl. $C_1$-to-$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$-to-$C_6$ alkyl amines and secondary $C_1$-to-$C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of the invention may be prepared according to conventional methods.

The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems", Vol 14 of the A. C. S. Symposium Series, and in *Bioreversible Carriers in Drug Design*, ed. Edward B. Roche, American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexylcarbodiimede) method, the active ester method (p-nitrophenyl ester method, N-hydroxysuccinic acid imide ester method, cyanomethyl ester method and the like), the Woodward reagent K method, the DCC-HOBT (1-hydroxy-benzotriazole) method and the like. Classical methods for amino acid condensation reactions are described in "Peptide Synthesis" Second Edition, M. Bodansky, Y. S. Klausnet and M. A. Ondetti (1976).

As in conventional peptide sysnthesis, branched chain amino and carboxyl groups at alpha and omega positions in amino acids may be protected and deprotected if necessary. The protecting groups for amino groups which can be used involve, for example, benzyloxycarbonyl (Z), o-chlorobenzyloxycarbonyl ((2-Cl)Z), p-nitrobenzyloxycarbonyl (Z($NO_2$)), p-methoxybenzyloxycarbonyl (Z(OMe)), t-amyloxycarbonyl (Aoc), isobornealozycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt) and dimethylphosphino-thioyl (Mpt).

The examples for protecting groups for carboxyl groups involve, for example, benzyl ester (OBzl), cyclohexyl ester, 4-nitrobenzyl ester (OBzlNO$_2$), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (NG) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mts) and the like; the thiol group in cysteine may be protected with benzyl, p-methoxybenzyl, triphenylmethyl, acetamidomethyl, ethylcarbamyl, 4-methylbenzyl (4-MeBzl), 2,4,6-trimethylbenzyl (Tmb) and the like; and the hydroxy group in serine may be protected with benzyl (Bzl), t-butyl, acetyl, tetrahydropyranyl (THP) and the like.

Numerous asymmetric centers may exist in the compounds of the present invention. Except where otherwise noted, the present invention contemplates the various stereoisomers and mixtures thereof. Accordingly, whenever a bond is represented by a wavy line, it is intended that both steric orientations are intended.

It should also be noted that certain variable elements of the structural formulae herein, such as the radicals $R^{11}$ and $R^{12}$ or the integers m, s and t, may appear more than once in a particular formula. In such instances, it is intended that, within a single formula, the values of these variables may be the same or different at each occurrence.

The compounds of the invention, including but not limited to those specified in the examples, possess immunomodulatory activity in animals. As immunosuppressants, the compounds of the present invention are useful when administered for the prevention immune-mediated tissue or organ graft rejection. Examples of transplanted tissues and organs which suffer from these effects are heart, kidney, liver, lung, small-bowel, and the like. The regulation of the immune response by the compounds of the invention would also find utility in the treatment of autoimmune diseases, such as rheumatoid arthritis, Hashimoto's thyroiditis, multiple sclerosis, myasthenia gravis, type I diabetes, uveitis, allergic encephalomyelitis, glomerulonephritis, and the like.

Further uses include the treatment and prophylaxis of inflammatory and hyperproliferative skin diseases and cutaneous manifestations of immunologically-mediated illnesses, such as psoriasis, atopical dermatitis, and Epidermolysis bullosa. Further instances where a compound of the invention would be useful include various eye diseases (autoimmune and otherwise) such as ocular pemphigus, Scleritis, and Graves' opthalmopathy, etc.

Other treatable conditions would include but are not limited to intestinal inflammations/allergies such as Crohn's disease and ulcerative colitis; renal diseases such as interstitial nephritis; hematic diseases such as aplastic anemia, idiopathic thrombocytopenic purpura, and autoimmune hemolytic anemia; skin diseases such as dermatomyositis; circulatory diseases such as myocardosis; collagen diseases such as Wegener's granuloma; nephrotic syndrome such as glomerulonephritis; Pyoderma; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, viral hepatitis, shock or anoxia).

When used in the above or other treatments, a therapeutically effective amount of one of the compounds of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat gastrointestinal disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to star doses of the compound at levels lower than required for to achieve the desired therapeutic effect and to gradually increase the dosage until the desired effect is achieved.

The total daily dose of the compounds of this invention administered to a human or lower animal may range from about 0.00 1 to about 3 mg/kg/day. For purposes of oral administration, more preferable doses may be in the range of from about 0.005 to about 1.5 mg/kg/day. If desired, the effective daily dose may be divided into multiple doses for purposes of administration; consequently, single dose compositions may contain such amounts or submultiples thereof to make up the daily dose.

The pharmaceutical compositions of the present invention comprise a compound of the invention and a pharmaceutically acceptable carder or excipient, which may be administered orally, rectally, parenterally, intracisternally, intravaginally, intraperitoneally, topically (as by powders, ointments, drops or transdermal patch), bucally, or as an oral or nasal spray. By "pharmaceutically acceptable carder" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drag in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology,* Volume XIV, Academic Press, New York, N.Y. (1976), p. 33 et seq.

The compounds of the invention may be prepared using one or more of the processes which follow. The starting materials for use in these processes are preferably one of the macrotides isolated from culture media obtained in accordance with known methods by fermentation of microorganisms of the genus Streptomyces, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on April 27, 1989 with the Agricultural Research Culture Collection International Depository, Peoria, Ill. 61604, USA under the provisions of the Budapest Treaty, under deposit No. NRRL 18488. The macrolide FR-900520 (European Patent Application 0184 162), also known as ascomycin, may be prepared in accordance to the published methods of (i) H. Hatanaka, M. Iwami, T. Kino, T. Goto and M. Okuhara, FR-900520 and FR-900523, *Novel immunosuppressants isolated from A streptomyces. I. Taxonomy of the producing strain. J. Antibiot.,* 1988. XLI(11), 1586–1591; (ii) H. Hatanaka, T. Kino, S. Miyata, N. Inamura, A. Kuroda, T. Goto, H. Tanaka and M. Okuhara, FR-900520 and FR-900523, *Novel immunosuppressants isolated from A streptomyces. II. Fermentation, isolation and physico-chemical and biological characteristics. J. Antibiot.,* 1988. XLI(11), 1592–1601; (iii) T. Arai, Y. Koyama, T. Suenaga and H. Honda, Ascomycin, *An Antifungal Antibiotic. J. Antibiot.,* 1962, 15(231–2); and (iv) T. Arai in U.S. Pat. No. 3,244,592. One or more of the processes discussed below may be then employed to produce the desired compound of the invention.

Such processes comprise:

(a) producing a compound of formula I, which contains bis(CH—OR) groups, in a corresponding compound wherein R is a protecting group.

(b) producing a compound of formula I, which contains a mono(CH—OR) group, by selective deprotection in a corresponding compound wherein R is a protecting group.

(c) producing a compound of formula I, which contains a CH—OR group, by selective activation of a selected CH—OH group in a corresponding compound wherein —OR is a leaving group which is easily displaced by nucleophilic attack.

(d) producing a compound of formula I, which contains a CH—$R^{100}$ group, by selective displacement of a selected CH—OR group in a corresponding compound wherein —$R^{100}$ is a nucleophile.

(e) producing a compound of formula I, which contains a CH—OH group, by selective and final deprotection in a corresponding compound.

In process (a), suitable protecting groups for hydroxyl include those groups well known in the art such as dimethylthexylsilyl, trisubstituted silyl such as tri(lower)alkylsilyl (e.g. trimethylsilyl, triethylsilyl, tributylsilyl, tri-i-propylsilyl, tert-butyl-dimethylsilyl, tri-tert-butylsilyl, triphenylmethyl-dimethylsilyl, etc.); lower alkyldiarylsilyl (e.g. methyl-diphenylsilyl, ethyl-diphenylsilyl, propyl-diphenylsilyl, tert-butyl-diphenylsilyl, etc.), and the like; triarysilyl (e.g. triphenylsilyl, tri-p-xylylsilyl, etc.); triarylalkylsilyl (e.g. tribenzylsilyl, etc.), and the like, in which the preferred one may be tri($C_1$-to-$C_4$)alkylsilyl and $C_1$-to-$C_4$ alkyldiphenylsilyl, and the most preferred one may be tert-butyldimethylsilyl;

Suitable o-silylations may be carried out using a wide variety of organosilicon reagents such as, but not liminted to tert-butyldimethylsilyl chloride, N-(tert-butyldimethylsilyl)-N-methyltrifluoroacetamide (Mawhinney, T., and Madison, M. A. *J. Org. Chem.,* 1982, 47, 3336), tert-butylchlorodiphenylsilane (Hanessian, S. and Lavallee, P *Can. J. Chem.,* 1975, 63, 2975), tert-butyldimethylsilyl trifluoromethanesulfonate (Mander, L. N. and Sethi, S. P. *Tetrahedron Lett.,* 1984, 25, 5953), dimethylthexylsilyl chloride or dimethylthexylsilyl trifluoromethanesulfonate (Wetter, H. and Oertle, K. *Tetrahedron Lett.,* 1985, 26, 5515), 1-(tert-butyldimethylsilyl)-imidazole and the like.

Carbonate hydroxy-protecting groups may be introduced using a wide variety of a haloformates such as methy, ethyl, 2,2,2-trichloroethyl, isobutyl, vinyl, allyl, 2-(trimethylsilyl-)ethyl, 2-(benzenesulfonyl)ethyl, 2-(trimethylsilyl)ethoxy methyl, benzyl and substituted benzyl chloroformates, where benzyl substituents include p-methoxy, 3,4-dimethoxy and p-nitro, in the presence of tertiary base such as pyridine, triethylamine, imidazole, diisopropylethylamine and the like. (*Tetrahedron Lett.,* 1980, 21, 3343; ibid., 1981, 22, 3667; ibid. 1981, 22,969; ibid. 1981, 22, 1933.)

The reaction may be carried out in a solvent which does not adversely affect the reaction (e.g., diethylether, dichloromethane, tetrahydrofuran, chloroform or N,N-dimethylformamide or a mixture thereof). The reaction may require cooling or heating, depending on the activation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, lutidine, picoline, 4-N,N-dimethylaminopyridine, etc.), quinoline, and the like, preferably in the presence of organic bases such as imidazole, triethylamine or pyridine.

The reaction may also be carried out using a starting material having an opposite configuration at a carbon center. In this situation, the following two additional steps are required to yield a starting material having an epimeric hydroxyl moiety, i.e. (1) the alcohol is oxidized to its corresponding ketone, (2) the obtained ketone is reduced under selective conditions. Both chiral centers having either [R]- or [S]-configuration can be obtained selectively and separately.

In process (b), suitable reagents for selective deprotection of a protecting group from C-32 may be carefully carded out using, but not limitted to aqueous hydrogen fluoride in acetonitrile (Newton, R. F., Reynolds, D. P., Finch, M. A. W., Kelly, D. R. and Roberts, S. M. *Tetrahedron Lett.*, 1979, 3891 ), tetraalkyl ammonium fluoride in tetrahydrofuran (Corey, E. J. and Snider, B. B. *J. Am. Chem. Soc.*, 1972, 94, 2549, Corey, E. J. and Venkateswarlu, A. *J. Am. Chem. Soc.*, 1972, 94, 6190) or tetraalkyl ammonium chloride-potassium fluoride in acetonitrile (Carpino, L. A. and Sau, A. C. *J. Chem. Soc., Chem. Commun.* 1979, 514) whererin an alkyl group as defined above, p-toluenesulfonic acid, potassium carbonate in anhydrous methanol (Hurst, D. T. and Malnnes, A. G. *Can. J. Chem.*, 1965, 43, 2004), citric acid in methanol (Bundy, G. L. and Peterson, D.C. *Tetrahedron Lett.*, 1978, 41), acetic acid:water (3:1) (Corey, E. J. and Varma, R. K. *J. Am. Chem. Soc.*, 1971, 93, 7319), Dowex 50W-X8 in methanol (Corey, E. J., Ponder, J. W. and Ulrich, P. *Tetrahedron Lett.*, 1980, 21, 137), boron trifluoride etherate in chloroform (Kelly, D. R., Roberts, M. S. and Newton, R. F. *Synth. Commun.* 1979, 9, 295), methanolic hydrogen fluoride (Hanessian, S. and Lavallee, P. *Can. J. Chem.*, 1975, 53, 2975; ibid., 1977, 55, 562), and pyridinuim fluoride in tetrahydrofuran (Nicolaou, K. C., Seitz, S. P., Pavia, M. R. and Petasis, N. A. *J. Org. Chem.*, 1979, 44, 4011 ), pyridinium p-toluenesulfonate in ethanol (Prakash, C., Saleh, S. and Blair, I. A. *Tetrahedron Lett.*, 1989, 30, 19), N-bromosuccinimide in dimethylsulfoxide (Batten, R. J. et al., *Synthesis*, 1980, 234), and tetraethyldiboroxane in the presence of catalytic amounts of trimethylsilyl triflate (Dahlhoff, W. V. and Taba, K. M., *Synthesis*, 1986, 561).

The reaction is usually conducted under from cooling to heating, preferably from 0° C. to 50° C. The reaction may require 20 minutes to one day, depending on the reagent and temperature chosen.

In process (c), suitable reagents for activation of an alcohol include acetic anhydride, trifluoromethanesulfonic anhydride (triflic anhydride), fluorosulfonic anhydride, methanesulfonyl chloride (mesyl chloride), p-toluenesulfonyl chloride (tosyl chloride), trifluoroacetic anhydride, trifluoroacetyl chloride, o-nitrobenzenesulfonyl chloride, 1-methyl-2-fluoropyridinium salt and the like.

The activation may be carried out in a solvent which does not adversely affect the reaction (e.g., diethylether, dichloromethane, tetrahydrofuran, chloroform or N,N-dimethylformamide or a mixture thereof). The reaction may require cooling or heating, depending on the activation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, lutidine, picoline, 4-N,N-dimethylaminopyridine, etc.), quinoline, and the like, preferably in the presence of organic bases such as triethylamine or pyridine.

The reaction is usually conducted under from cooling to heating, preferably from −70° C. to 50° C. The reaction may require 20 minutes to one day, depend on the reagent and temperature chosen.

In process (d), a variety of compounds may be prepared from the displacement reactions. An activated hydroxyl group may be reacted with a primary or secondary amine (as defined above and below). The displacement reaction may be carded out in a solvent which does not adversely affect the reaction (e.g. chloroform, dichloromethane, tetrahydrofuran, pyridine, dimethylsulfoxide, N,N-dimethylformamide, hexamethylphosphoramide, etc. or a mixture thereof). The reaction may be conducted above, at, or below ambient temperature, preferably from 0° C. to 50° C. The reaction may require 20 minutes to one week, depend on the reagent chosen.

In process (e), a final deprotection of C-24 protecting group may be carried out according to the method described in process (c).

The compounds, processes and uses of the present invention will be better understood in connection with the following examples, which are intended as an illustration of and not a limitation upon the scope of the invention. Both below and throughout the specification, it is intended that citations to the literature are expressly incorporated by reference.

EXAMPLE 1

Formula I: $R^{100}$=H; $R^{101}$=ethyl; $R^{102}$=H;
$R^{103}$=tert-butyldimethylsilyloxy;
$R^{104}$=tert-butyldimethylsilyloxy; $R^{105}$=H Ascomycin (25 g, 0.032 mol) was dissolved in a solution of imidazole (43.03 g, 0.64 mol) in dry N,N-dimethylformamide (500 mL) and tert-butyldimethylchlorosilane (47.64 g, 0.32 mol) was added in portions and stirred at room temperature for 24 hours. N,N-dimethylformamide and excess tert-butyldimethylchlorosilane were removed by evaporation (35° C. water bath) under high vaccum. The solid residue was dissolved in 350 mL of ethyl acetate, and the ethyl acetate layer was washed with saturated ammonium chloride aqueous solution (200 mL×3), 10%-NaHSO$_4$ (200 mL×3), brine, saturated NaHCO$_3$ (200 mL×3), and brine (200 mL×3). After dired over MgSO$_4$, solvent was removed in vacuo and the solid residue was purified by silica gel chromatography, followed by HPLC eluting with 5% acetone in hexane providing the title compound (27 g) in 84% yield. MS (FAB) m/z: M+K=1058.

EXAMPLE 2

Formula I: $R^{100}$=H; $R^{101}$=ethyl; $R^{102}$=H;
$R^{103}$=tert-butyldimethylsilyloxy; $R^{104}$=OH; $R_{10}$=H To a solution of 48% hydrogen fluoride aqueous solution (5 mL) was added Example 1 (32 g, 0.031 mol) in acetonitrile (500 mL), and the mixture was stirred at room temperature for 90 minutes. It was cooled to 0° C. in an ice bath, and solid NaHCO$_3$ was added to the reaction mixture. It was stirred for 1 hour and solid was removed by filtration. Acetonirile was removed in vacuo and ethyl acetate (500 mL) was added to tthe residue, and the organic layer was washed with 10%-NaHCO$_3$ (300 mL×3), brine (250 mL), 10%-NaHSO$_4$ (300 mL×3), and brine (350 mL×3), and dried over anhydrous sodium sulfate. Evaporation of the solvent gave 35 g of crude title compound which was purified by silica gel column chromatography, followed by HPLC eluting with 25%-acetone in hexane. 24.28 g (85%) of pure compound was obtained. MS (FAB) m/z: M+K=844; In addition to the title compound, unreacted starting material (Example 1, 1.5 g) and ascomycin (500 mg) were isolated as a pure form.

EXAMPLE 3

Formula I: $R^{100}$=H; $R^{101}$=ethyl; $R^{102}$=H; $R^{103}$=tert-butyldimethylsilyloxy: $R^{104}$=O-trifluoromethanesulfonyl; $R^{105}$=H The product of Example 2 (4.0 g, 4.42 mmol) was dissolved in 20 mL of methylene chloride at 0° C. pyridine (3.57 mL, 44.2 mmol), followed by trifluoromethanesulfonic acid anhydride (0.74 mL, 4.42 mmol) were carefully added to the reaction mixture. It was stirred at 0° C. for 20 minutes and the solvent was removed. Ethyl acetate (50 mL) was added to the residue. The organic layers were washed with brine, saturated NaHCO$_3$ (20 mL×3), brine (20 mL), 10%-NaHSO$_4$ (20 mL×3), brine (20 mL×3) and dried over anhydrous sodium sulfate. After the solvent was removed, the title compound was obtained in quantitative yield (4.2 g). This compound was used for the displacement reaction without further purification and characterization.

EXAMPLE 4

Formula I: $R^{100}$=H; $R^{101}$=ethyl; $R^{102}$=H; $R^{103}$=tert-butyldimethylsilyloxy; $R^{104}$=H; m=0; n=1; $R^3$=$R^4$=$R^5$=H; $R^1$=methyl The product of Example 3 (2.1 g, 2.03 mmol) was dissolved in 10 mL of freshly distilled methylene chloride, 1-methylpiperazine (1.24 mL, 10.15 mmol) and triethylamine (0.85 mL, 6.09 mmol) were added, and the reaction was then stirred at 50° C. for 5 hours and at room temperature for one over night. The reaction mixture was directly poured onto silica gel column and eluted to obtain semi-pure title compound (925 mg) in 46% yield. MS (FAB) m/z: M+K=1026. M+H=988.

EXAMPLE 5

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=methyl The product of Example 4 (920 mg, 0.93 mmol) was dissolved in 10 mL of acetonitrile:water (9:1), 48% hydrogen fluoride aqueous solution [48%-HF] (0.6 mL) was added, and the reaction was then stirred at room temperature for 5 hours. It was cooled to 0° C. in an ice bath, and solid NaHCO$_3$ was added to the reaction mixture. It was stirred for 0.5 hour and solid was removed by filtration. Acetonirile was removed in vacuo and the residue was purified by reverse phase HPLC (RP-HPLC), eluting with acetonitrile-water-0.01% trifluoroacetic acid system. 290 mg of pure title compound was obtained. MS (FAB) m/z: M+H=874, M+K =912; mp=132° C. (dec.)

EXAMPLE 6

Formula I: $R^{100}$=H; $R^{110}$=ethyl; $R^{102}$=H; $R^{103}$=tert-butyldimethylsilyloxy; $R^{104}$=H; m=0; n=1; $R^3$=$R^4$=$R^5$=H; $R^1$=benzyl The product of Example 3 (2.1 g, 2.03 mmol) was dissolved in 8 mL Of freshly distilled methylene chloride, 1-benzylpiperazine (1.06 mL, 6.1 mmol) and triethylamine (0.85 mL, 6.1 mmol) were added, and was then stirred at 45° C. for 5 hours. The reaction mixture was directly poured onto silica gel column and eluted to obtain semi-pure title compound (1.52 g). It was then purified by HPLC, eluting with 30% acetone-hexane. 660 mg of pure title compound was isolated in 31% yield. MS (FAB) m/z: M+K=1102. M+H=1064.

EXAMPLE 7

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=benzyl The product of Example 6 (1.3 g, 1.22 mmol) was dissolved in 35 mL of acetonitrile, 48% hydrogen fluoride aqueous solution [48%-HF] (2.2 mL) was added, and the reaction was then stirred at room temperature for 8 hours. The reaction was quenched by the addition of saturated NaHCO$_3$ solution and the product was extracted with 50 mL of ethyl acetate (x2). The ethyl acetate layer was washed with 10%-NaHCO$_3$, brine and dried over anhydrous sodium sulfate. Evaporation of the solvent gave 1 g of crude tile compound was obtained. This was purified by RP-HPLC, eluting with acetonitrile-water-0.01%-trifluoroacetic acid system. 330 mg of the pure title compound was obtained. MS (FAB) m/z: M+H =950, M+K=988; mp=114°–116° C.

EXAMPLE 8

Formula I: $R^{100}$=H; $R^{101}$=ethyl; $R^{102}$=H; $R^{103}$=tert-butyldimethylsilyloxy; $R^{104}$=H; m=0; n=1; $R^3$=$R^4$=$R^5$=H; $R^1$=phenyl Following the procedure of Example 6, but replacing 1-benzylpiperazine with 1-phenylpiperazine, provided the desired compound. The product of Example 3 (2.1 g, 2.03 mmol), 1-penylpiperazine (1.53 mL, 6.07 mmol), and triethylamine (1.17 mL, 5.05 mmol) in 10 mL of methylene chloride were used. 660 mg of the pure title compound was isolated in 32% yield. MS (FAB) m/z: M+K=1088. M+H= 1050.

EXAMPLE 9

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=phenyl Following the procedure of Example 5, the product of Example 8 (250 mg, 0.24 mmol), 48%-HF (0.5 mL) in 10 mL of acetonitrile were used. 202 mg of the pure title compound was isolated after purified by RP-HPLC. MS (FAB) m/z: M+K=974. M+H=936. mp=119° C. (dec.)

EXAMPLE 10

Formula I: $R^{100}$=H; $R^{101}$=ethyl; $R^{102}$=H; $R^{103}$=tert-butyldimethylsilyloxy; $R^{104}$=H; m=0; n=1; $R^3=R^4=R^5$H; $R^1$=tert-butyloxycarbonyl Following the procedure of Example 6, but replacing 1-benzylpiperazine with 1-tert-butyloxycarbonylpiperazine, provided the desired compound. The product of Example 3 (2.1 g, 2.03 mmol), 1-tert-butyloxycarbonylpiperazine (1.13 g, 6.09 mmol), and triethylamine (0.85 mL, 6.09 mmol) in 10 mL of methylene chloride were used. 670 mg of the pure title compound was isolated in 31% yield. MS (FAB) m/z: M+K=1112. M+H=1074.

EXAMPLE 11

Formula I: $R^{100}$=H; $R^{101}$=ethyl; $R^{102}$=H; $R^{103}$=OH; $R^{104}$=H; m=0; n=1; $R^3=R^4=R^5$=H; $R^1$=tert-butyloxycarbonyl Following the procedure of Example 5, the product of Example 10 (660 mg, 0.65 mmol), 48%-HF (3 mL) in 30 mL of acetonitrile were used. 279 mg of the pure title compound was isolated after purified by RP-HPLC. MS (FAB) m/z: M+K=998.

EXAMPLE 12

Formula I: $R^{100}$=H; $R^{101}$=ethyl; $R^{102}$=H; $R^{103}$=OH; $R^{104}$=H; m=0; n=1; $R^3=R^4=R^5$=H; $R^1$=[4-nitrobenzyl]

Following the procedure of Example 6, but replacing 1-benzylpiperazine with 1-[4-nitrobenzyl]piperazine, provided the desired compound. To a solution of piperazine (2 g, 0.023 mol) in 10 mL of ethanol added a solution of 4-nitrobenzyl bromide (5 g, 0.023 mol) in 20 mL of warm ethanol. It was gently refluxed for 1 hour and stirred at room temperature for one over night. The resulting white precipitate was filtered, washed with a small amount of cold ethanol, and dried to yield 1-[4-nitrobenzyl]piperazine hydrobromide (3 g). MS m/z M+H=222, $H^1$-NMR (in MeOH-$d_4$) δ=2.7 (t, 4H, piperazine), 3.25 (t, 4H, piperazine), 3.75 (s, 2H, benzyl), 7.62 (d, 2H, aromatic), 8.20 (d, 2H, aromatic). The obtained 1-[4-nitrobenzyl]piperazine hydrobromide (3 g, 9.93 mmol) was dissolved in 60 mL of 3N sodium hydroxide aqueous solution and stirred at room temperature for 30 minutes. The product was extracted with ethyl acetate (50 mL×3), and the combined ethyl acetate layer was washed with brine, dried over anhydrous sodium sulfate. Solvent was removed to obtain 1.7 g of 1-[4-nitrobenzyl]piperazine in 78% yield. MS m/z M+H=222, $H^1$-NMR (in MeOH-$d_4$) δ2.45 (t, 4H, piperazine), 2.90 (t, 4H, piperazine), 3.55 (s, 2H, benzyl), 7.52 (d, 2H, aromatic), 8.50 (d, 2H, aromatic). The product of Example 3 (2.1 g, 2.03 mmol), 1-[4-nitrobenzyl]piperazine (1.7 g, 8.1 mmol), and triethylamine (0.85 mL, 6.09 mmol) in 10 mL of methylene chloride were used. The reaction was carried out at 45° C. for 15 hours. 1.07 g of semi-pure compound was isolated in 48% yield. MS (FAB) m/z: M+K=1147. M+H= 1109. The obtained product (1.0 g, 0.9 mmol) was treated with 48%-HF (4 mL) in 30 mL of acetonitrile in the procedure described in Example 5, except stirred at 45° C. for 3 hours. 554 mg of the pure title compound was isolated in 50% yield after RP-HPLC. MS (FAB) m/z: M+K=1033. M+H=996. mp=113° C. (dec.)

EXAMPLE 13

Formula I: $R^{100}$=H; $R^{101}$=ethyl; $R^{102}$=H; $R^{103}$=OH; $R^{104}$=H; m=0; n=1; $R^3=R^4=R^5$=H; $R^1$=β-naphthylmethyl Following the procedure of Example 6, but replacing 1-benzylpiperazine with 1-β-naphthylmethylpiperazine, provided the desired compound. To a solution of piperazine (2.0 g, 0.023 mol) in 15 mL of ethanol added a solution of (2-bromomethyl)naphthalene (5 g, 0.023 mol) in 15 mL of warm ethanol. It was stirred at 55° C. for 1 hour and stirred at room temperature for one over night. The resulting precipitate was filtered, washed with ethyl acetate (20 mL×2), and dried to yield 1-naphthylmethylpiperazine hydrobromide (2.3 g). MS m/z M+H=227, $H^1$-NMR (in MeOH-$d_4$) δ=2.85 (t, 4H, piperazine), 3.20 (t, 4H, piperazine), 3.72 (s, 2H, benzyl), 7.45 (m, 3H, aromatic), 7.70 (s, 2H, aromatic), 7.80 (3, 3H, aromatic). The obtained 1-naphthylmethylpiperazine hydrobromide (2.2 g, 7.16 mmol) was dissolved in 50 mL of 3N sodium hydroxide aqueous solution and stirred at room temperature for 30 minutes. The product was extracted with ethyl acetate (50 mL×3), and the combined ethyl acetate layer was washed with brine, dried over anhydrous sodium sulfate. Solvent was removed to obtain 1.2 g of 1-[naphthylmethyl]piperazine in 75% yield. MS m/z M+H=227, $H^1$-NMR (in MeOH-$d_4$) δ=2.5 (m, 4H, piperazine), 2.95 (t, 4H, piperazine 3.55 (s, 2H, benzyl), 7.74 (m, 3H, aromatic), 7.72 (s, 2H, aromatic), 7.79 (m, 3H, aromatic). The product of Example 3 (2.1 g, 2.03 mmol), 1-naphthylmethylpiperazine (1.84 g, 8.1 mmol), and triethylamine (0.85 mL, 6.09 mmol) in 10 mL of methylene chloride were used. 860 mg of pure compound was isolated in 38% yield. MS (FAB) m/z: M+H=1114. The obtained product (850 mg, 0.76 mmol) was treated with 48%-HF (4 mL) in 30 mL of acetonitrile in the procedure described in Example 5. 413 mg of the pure title compound was isolated after purified by RP-HPLC in 41% yield. MS (FAB) m/z: M+K=1038. M+H=1000. mp=125°–126° C.

EXAMPLE 14

Formula I: $R^{100}$=H; $R^{101}$=ethyl; $R^{102}$=H; $R^{103}$=OH; $R^{104}$=H; m=0; n=1; $R^2=R^{2'}=R^3=R^4=R^5$=H Following the procedure of Example 6, but replacing 1-benzylpiperazine with piperidine, provided the desired compound. The product of Example 3 (2.1 g, 2.03 mmol), piperidine (0.6 mL, 6.09 mmol), and triethylamine (0.85 mL, 6.09 mmol) in 10 mL of methylene chloride were used. 1.01 g of pure compound was isolated in 55% yield. MS (FAB) m/z: M+H=973. M+K=1011. The obtained product (1.0 g, 1.03 mmol) was treated with 48%-HF (3 mL) in 40 mL of acetonitrile in the procedure described in Example 5. 560 mg of the pure title compound was isolated in 56% yield. MS (FAB) m/z: M+K=897. M+H=859. mp=100°–101° C.

EXAMPLE 15

Formula I: $R^{100}$=H; $R^{101}$=ethyl; $R^{102}$=H; $R^{103}$=OH; $R^{104}$=H; m=0; n=1; $R^3=R^4=R^5$=H; $R^1$=formyl Following the procedure of Example 6, but replacing 1-benzylpiperazine with 1-piperazinecarboxaldehyde, provided the desired compound. The product of Example 3 (2.1 g, 2.03 mmol), 1-piperazinecarboxaldehyde (0.62 mL, 6.09 mmol), and triethylamine (0.85 mL, 6.09 mmol) in 10 mL of methylene chloride were used. It was stirred at 45° C. for 15 hours. 270 mg of pure compound was isolated in 13% yield. MS (FAB) m/z: M+H=1002. M+K=1040. The obtained product (260 mg, 0.26 mmol) was treated with 48%-HF (1 mL) in 15 mL of acetonitrile in the procedure described in Example 5. 176 mg of the pure title compound was isolated in 68% yield. MS (FAB) m/z: M+H=888. M+K=926. mp=126°–128° C.

EXAMPLE 16

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^2$ and $R^{2'}$ taken together to form —O(CH$_2$)$_i$O— wherein i=2

Following the procedure of Example 6, but replacing 1-benzylpiperazine with 4-piperidone ethylene ketal, provided the desired compound. The product of Example 3 (2.0 g, 1.9 mmol), 4-piperidone ethylene ketal (0.742 mL, 5.7 mmol), and triethylamine (0.81 mL, 6.09 mmol) in 10 mL of methylene chloride were used. 1.03 g of pure compound was isolated in 54% yield. MS (FAB) m/z: M+H=1031. M+K=1069. The obtained product (1.0 g, 0.97 1 mmol) was treated with 48%-HF (3 mL) in 35 mL of acetonitrile in the procedure described in Example 5. 574 mg of the pure title compound was isolated in 57% yield. MS (FAB) m/z: M+H=917. M+K=955. mp=109°–110° C.

EXAMPLE 17

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-hydroxyethyl Following the procedure of Example 6, but replacing 1-benzylpiperazine with 1-[2-hydroxyethyl]piperazine, provided the desired compound. The product of Example 3 (2.0 g, 1.9 mmol), 1-[2-hydroxyethyl]piperazine (0.71 mL, 5.7 mmol), and triethylamine (0.81 mL, 5.7 mmol) in 10 mL of methylene chloride were used. 970 mg of pure compound was isolated in 49% yield. MS (FAB) m/z: M+H=1018. M+K=1056. The obtained product (960 mg, 0.94 mmol) was treated with 48%-HF (4 mL) in 40 mL of acetonitrile in the procedure described in Example 5. 414 mg of the pure title compound was isolated in 49% yield. MS (FAB) m/z: M+H=904. M+K=942.

EXAMPLE 18

Formula I: $R^{100}$=H; $R^{101}$=ethyl; $R^{102}$=H; $R^{103}$=OH; $R^{104}$=H; m=0; n=1; $R^3$=$R^4$=$R^5$=H; X=oxygen Following the procedure of Example 6, but replacing 1-benzylpiperazine with morpholine, provided the desired compound. The product of Example 3 (2.0 g, 1.9 mmol), morpholine (0.51 mL, 5.7 mmol), and triethylamine (0.81 mL, 5.7 mmol) in 10 mL of methylene chloride were used. 780 mg of pure compound was isolated in 42% yield. MS (FAB) m/z: M+H=975. M+K=1013. The obtained product (780 mg, 0.80 mmol) was treated with 48%-HF (3 mL) in 35 mL of acetonitrile in the procedure described in Example 5. 457 mg of the pure title compound was isolated in 59% yield. MS (FAB) m/z: M+H=861. M+K=899. mp=107°–108° C.

EXAMPLE 19

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-(2-hydroxyethoxy)ethyl Following the procedure of Example 6, but replacing 1-benzylpiperazine with 1-[2-(2hydroxyethoxy)ethyl]piperazine, provided the desired compound. The product of Example 3 (2.1 g, 2.03 mmol), 1-{2-(2-hydroxyethoxy)ethyl]piperazine (0.998 mL, 6.09 mmol), and triethylamine (0.85 mL, 6.09 mmol) in 10 mL of methylene chloride were used. 1.2 g of pure compound was isolated in 56% yield. MS (FAB) m/z: M+H=1062. M+K=1100. The obtained product (1.2 g, 1.13 mmol) was treated with 48%-HF (4 mL) in 35 mL of acetonitrile in the procedure described in Example 5, except reaction time was 2.5 hours. 580 mg of the pure title compound was isolated in 53% yield. MS (FAB) m/z: M+H=948. M+K=986. mp=102°–104° C.

EXAMPLE 20

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-pyridyl Following the procedure of Example 6, but replacing 1-benzylpiperazine with 1-(2-pyridyl)piperazine, provided the desired compound. The product of Example 3 (2.0 g, 1.93 mmol), 1-(2-pyridyl)piperazine (0.881 mL, 5.79 mmol), and triethylamine (0.81 mL, 5.79 mmol) in 10 mL of methylene chloride are used and stirred at 45° C. for one over night. 580 mg of pure compound was isolated after silica gel column chromatography, followed by normal phase HPLC purification in 29% yield. MS (FAB) m/z: M+H=1051. M+K=1089. The obtained product (570 mg, 0.543 mmol) was treated with 48%-HF (4 mL) in 25 mL of acetonitrile in the procedure described in Example 5, except reaction time was 4 hours. 400 mg of the pure title compound was isolated in 63% yield. MS (FAB) m/z: M+H =937. M+K=975. mp=110° C. (dec.).

EXAMPLE 21

Formula I: $R^{100}$=H; $R^{101}$=ethyl; $R^{102}$=H; $R^{103}$=H; $R^{104}$=H; m=0; n=1; $R^3$=$R^4$=$R^5$=H; $R^1$=2-pyrimidyl Following the procedure of Example 6, but replacing 1-benzylpiperazine with 1-(2-pyrimidyl)piperazine, provided the desired compound. The product of Example 3 (2.1 g, 2.03 mmol), 1-(2-pyrimidyl)piperazine (0.996 mL, 6.09 mmol), and triethylamine (0.85 mL, 6.09 mmol) in 10 mL of methylene chloride are used. 870 mg of pure compound was isolated after silica gel column chromatography, followed by normal phase HPLC purification in 41% yield. MS (FAB) m/z: M+H=1052. M+K=1090. The obtained product (0.86 g, 0.82 rental) was treated with 48%-HF (4 mL) in 30 mL of acetonitrile in the procedure described in Example 5, except reaction time was 3.5 hours. 380 mg of the pure title compound was isolated in 40% yield. MS (FAB) m/z: M+H =938. M+K=976. mp=110°–111° C.

EXAMPLE 22

Formula I: $R^{100}$=H; $R^{101}$=ethyl; $R^{102}$=H; $R^{103}$=OH; $R^{104}$=H; m=1; n=1; $R^1$=$R^3$=$R^4$=$R^5$=H Commercially available N-tert-butyloxycarbonyl-piperazine (0.5 g, 2.68 mmol) was dissolved in 5 mL of THF:water (1:1) and cooled in an ice bath. Triethylamine (0.748 mL, 5.4 mmol), followed by benzyloxycarbonyl chloride (0.575 mL, 3.21 mmol) in diethyl ether was slowly added to the reaction mixture. It was stirred at 0° C. for 1.5 hours. Solvents were removed and 50 mL of ethyl acetate was added to the residue. The ethyl acetate layer was washed with saturated $NaHCO_3$ (20 mL×3), brine (20 mL×3), and dried over anhydrous sodium sulfate. N-tert-butyloxycarbonyl-N;benzyloxycarbonyl-piperazine (1.0 g) was obtained after evaporated to dryness in quantitative yield. MS: $M+NH_4$=338. $M+H^+$=321. N-tert-butyloxycarbonyl-N'-benzyloxycarbonyl-piperazine (1.8 g, 3.13 mmol) was dissolved in 10 mL of 4N-HCl/dioxane. It was stirred at room temperature for 30 minutes. The reaction mixture was cooled in an ice bath, 1N-NaOH solution was carefully added to the mixture to adjust pH above 10. Ethyl acetate (50 mL×3) was used to extract the compound. The combined ethyl acetate layers were washed with brine, dried over anhydrous sodium sulfate. After removal of the solvent, 1.1 g of N-benzyloxycarbonyl-piperazine was obtained in quantitative yield. Following the procedure of Example 6, but replacing 1-benzylpiperazine with N-benzyloxycarbonyl-piperazine, provided the desired compound. The product of Example 3 (1.1 g, 1.06 mmol), N-benzyloxycarbonyl-piperazine (700 mg, 3.18 mmol), and triethylamine (0.44 mL, 3.15 mmol) in 5 mL of methylene chloride were used. 339 mg of pure compound (C-32-N-benzyloxycarbonyl-piperazinyl-C-24-TBDMS-Ascomycin) was isolated in 29% yield. MS (FAB) m/z: M+H=1108. M+K=1146. The above obtained product (329 mg, 0.297 mmol) was treated with 48%-HF (0.55 mL) in 10 mL of acetonitrile in the procedure described in Example 5. 316 mg of semi pure compound (C-32-N-benzyloxycarbonyl-piperazinyl-Ascomycin) was isolated. This was directly used for the next reaction without further purification. The obtained product (317 mg, 0.32 mmol) was carefully hydrogenated in 40 mL of methanol in the presence of 10%-palladium on charcoal until theoretical ammount of hydrogen gas was consumed. 290 mg of crude product was purified by reverse phase-HPLC. 117 mg of the pure title compound was obtained in 47% yield. MS (FAB) m/z: M+H=860. M+K=898. mp=132° C. (dec).

EXAMPLE 23

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=3-pyridyl 3-Bromopyridine (0.963 mL, 10 mmol) and piparazine (0.861 g, 10 mmol) are gently refluxed in 20 mL of absolute ethanol until the starting materials are disappeared on TLC. Ethanol is removed in vacuo to obtain 1-[3-pyridyl]piperazine hydrochloride. The hydrochloride salt is removed according to the procedure described in Example 22 to yield 1-[3-pyridyl]piperazine. Following the procedure of Example 6, but replacing 1-benzylpiperazine with 1-[3-pyridyl]piperazine, provides the desired compound. The product of Example 3 (2.1 g, 2.03 mmol), 1-[3-pyridyl] piperazine (6.09 mmol), and triethylamine (0.85 mL, 6.09 mmol) in 10 mL of methylene chloride are used. The obtained product (1.2 g, 1.13 mmol) is treated with 48%-HF (4 mL) in 35 mL of acetonitrile in the procedure described in Example 5. The pure title compound is isolated.

EXAMPLE 24

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=4-pyridyl 4-Bromopyridine hydrochloride (2.25 g, 11.61 mmol) and piparazine (5 g, 58.05 mmol) were dissolved in 10 mL of absolute ethanol and replaced into a sealed tube. It was kept in 95° C. oil bath for 5 hours and allowed to stand at room temperature for one over night. The white precipitate was filtered off, washed with a small amount of cold ethanol, and the filtrate was concentrated in vacuo to obtain 1-[4-pyridyl] piperazine hydrobromide hydrochloride salt with a contamination of unreacted piperazine. MS m/z M+H=165. $H^1$-NMR (in $CDCl_3$) δ=2.95 (m, 4H), 3.36 (t, 4H), 6.82 (2H, aromatic), 8.10 (2H, aromatic). The obtained 1-[4 -pyridyl] piperazine hydrobromide hydrochloride salt (1.0 g) was dissolved in 50 mL of 3N sodium hydroxide aqueous solution and stirred at room temperature for 15 minutes. The product was extracted with ethyl acetate (50 mL×3) and the combined ethyl acetate layer was washed with brine (50 mL×2), dried over anhydrous sodium sulfate. The solvent was removed in vacuo to obtain 450 mg of 1-[4-pyridyl] piperazine in 77% yield. MS m/z M+H=165. $H^1$-NMR (in $CDCl_3$) δ=3.00 (m, 4H), 3.30 (t, 4H), 6.65 (2H, aromatic), 8.25 (2H, aromatic). Following the procedure of Example 6, but replacing 1-benzylpiperazine with 1-[4-pyridyl]piperazine, provides the desired compound. The product of Example 3 (2.1 g, 2.03 mmol), 1-[4-pyridyl]piperazine (999 mg, 6.09 mmol), and triethylamine (0.85 mL, 6.09 mmol) in 10 mL of methylene chloride are used. The obtained product (1.2 g, 1.13 mmol) is treated with 48%-HF (4 mL) in 35 mL of acetonitrile in the procedure described in Example 5 to yield the pure title compound.

EXAMPLE 25

Formula I: $R^{100}$=H; $R^{101}$=ethyl, $R^{102}$=H; $R^{103}$=OH; $R^{104}$=H; m=0; n=1; $R^3$=$R^4$=$R^5$=H; $R^1$=methanesulfonyl N-tert-butyloxycarbonylpiperazine (1.0 g, 5.34 mmol) was dissolved in 5 mL of THF:water (1:1) and cooled in an ice bath. Triethylamine (1.45 mL, 10.68 mmol), followed by methanesulfonyl chloride (0.50 mL, 6.44 mmol) in 5 mL of ether were added, and stirred at 0° C. for 1 hour and at room temperature for 2 hours. Solvents were removed and 40 mL of ethyl acetate was added to the residue. The ethyl acetate layer was washed with brine (30 mL×3) and dried over anhydrous sodium sulfate. After filtered, the filtrate was concentrated in vacuo to yield 1.314 g of N-tert-butyloxycarbonyl-N'-methanesulfonyl-piperazine in 93% yield. MS m/z $M+NH_4$=282. $H^1$-NMR (in $CDCl_3$) δ=1.48 (s, 9H, Boc), 2.79 (s, 3H, S-$CH_3$), 3.18 (t, 4H, piperazine), 3.55 (t, 4H, piperazine). The obtained N-tert-butyloxycarbonyl-N'-methanesulfonyl-piperazine (1.3 g, 4.97 mmol) was dissolved in 10 mL of 20% trifluoroacetic acid in methylene chloride and stirred at room temperature for 30 minutes. Solvent and trifluoroacetic acid were removed to obtain N-methanesulfonylpiperazine trifluoroacetic acid salt in quantitative yield. MS m/z M+H=165, $H^1$-NMR (in MeOH-$d_4$) δ=2.95 (s, 3H, S-$CH_3$), 3.35 (m, 4H, piperazine), 3.5 (m, 4H, piperazine). The obtained N-methanesulfonylpiperazine trifluoroacetic acid salt (2.2 g) was dissolved in 30 mL of acetonitrile and cooled in an ice bath. Solid sodium bicarbonate was added to the acetonitrile solution and stirred for 2 hours. Solid was filtered off and the filtrate was concentrated in vacuo to yield N-methanesulfonylpiperazine in quantitative yield. MS m/z M+H=165, $M+NH_4$=182; $H^1$-NMR (in MeOH-$d_4$) δ=2.85 (s, 3H, S-$CH_3$), 2.95 (t, 4H, 3.22 (t, 4H, piperazine). Following the procedure of Example 6, but replacing 1-benzylpiperazine with 1-methanesulfonylpiperazine, provides the desired compound. The product of Example 3 (2.1 g, 2.03 mmol), base-treated salt free form of 1-methanesulfonylpiperazine (999 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to yield the pure title compound.

EXAMPLE 26

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=diethylphosphoryl N-tert-butyloxycarbonylpiperazine (1.0 g, 5.34 mmol) was dissolved in 5 mL of THF:water (1:1) and cooled in an ice bath. Triethylamine (1.45 mL, 10.68 mmol), followed by diethylchlorophosphate (1.16 mL, 8.01 mmol) in 5 mL of ether were added, and stirred at 0° C. for 1 hour and at room temperature for 2 hours. Solvents were removed and 40 mL of ethyl acetate was added to the residue. The ethyl acetate layer was washed with brine (30 mL×3) and dried over anhydrous sodium sulfate. After filtered, the filtrate was concentrated in vacuo to yield 1.5 g of N-tert-butyloxycarbonyl-N'-diethylphosphoryl-piperazine in 88% yield as an oil. MS m/z M+H=323, M+$NH_4$=340. $H^1$-NMR (in $CDCl_3$) δ=1.32 (t, 6H, 2×$CH_3$), 1.48 (s, 9H, Boc), 3.1 (m, 4H, piperazine), 3.37 (t, 4H, piperazine), 4.05 (m, 4H, 2×$OCH_2$). The obtained N-tert-butyloxycarbonyl-N'-diethylphosphoryl-piperazine (1.5 g, 4.66 mmol) was dissolved in 10 mL of 10% trifluoroacetic acid in methylene chloride and stirred at room temperature for 30 minutes. Solvent and trifluoroacetic acid were removed to obtain 1.6 g of N-diethylphosphorylpiperazine trifluoroacetic acid salt in quantitative yield. MS m/z M+H=223, $H^1$-NMR (in MeOH-$d_4$) δ=1.35 (m, 6H, 2×$CH_3$), 3.19 (m, 4H, piperazine) (m, 4H, piperazine), 4.05 (m, 4H, 2×$OCH_2$). Following the procedure of Example 6, but replacing 1-benzylpiperazine with 1-diethylphosphorylpiperazine, provides the desired compound. The product of Example 3 (2.1 g, 2.03 mmol), base-treated salt free form of N-diethylphosphorylpiperazine (1.358 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to yield the pure title compound.

EXAMPLE 27

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=1-pyrrolidinocarbonylmethyl Following the procedure of Example 6, but replacing 1-benzylpiperazine with 1-[1-pyrrolidinocarbonylmethyl]piperazine, provided the desired compound. The product of Example 3 (2.0 g, 1.93 mmol), 1-[1-pyrrolidinocarbonylmethyl]piperizine (1.14 g, 5.79 mmol), and triethylamine (0.81 mL, 5.79 mmol) in 10 mL of methylene chloride were used. 1.4 g of pure compound was isolated in 67% yield. MS (FAB) m/z: M+H=1085. M+K=1123. The obtained product (1.2 g, 1.11 mmol) was treated with 48%-HF (4 mL) in 45 mL of acetonitrile in the procedure described in Example 5, except reaction time was 3.5 hours. 620 mg of the pure title compound was isolated in 52% yield. MS (FAB) m/z: M+H=971. M+K=1009. mp=110°–112° C.

EXAMPLE 28

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=1-morpholinocarbonylmethyl Following the procedure of Example 6, but replacing 1-benzylpiperazine with 1-[1-morpholinocarbonylmethyl]piperazine, provided the desired compound. The product of Example 3 (2.0 g, 1.93 mmol), 1-[1-morpholinocarbonylmethyl]piperizine (1.23 g, 5.79 mmol), and triethylamine (0.81 mL, 5.79 mmol) in 10 mL of methylene chloride were used. 1.1 g of pure compound was isolated in 55% yield. MS (FAB) m/z: M+H=1101. The obtained product (1.0 g, 0.909 mmol) was treated with 48%-HF (4 mL) in 45 mL of acetonitrile in the procedure described in Example 5. 624 mg of the pure title compound was isolated in 56% yield. MS (FAB) m/z: M+H=987. M+K=1025. mp=112°–113° C.

EXAMPLE 29

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=cyclopropyl Following the procedure of Example 6, but replacing 1-benzylpiperazine with 1-cyclopropylpiperazine, provides the desired compound. The product of Example 3 (2.1 g, 2.03 mmol), 1-cyclopropylpiperazine (6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 30

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=cyclobutyl Following the procedure of Example 6, but replacing 1-benzylpiperazine with 1-cyclobutylpiperazine, provides the desired compound. The product of Example 3 (2.1 g, 2.03 mmol), base-treated free base form of 1-cyclobutylpiperazine (854 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 31

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=cyclopentyl Following the procedure of Example 6, but replacing 1-benzylpiperazine with 1-cyclopentylpiperazine, provided the desired compound. The product of Example 3 (2.1 g, 2.03 mmol), base-treated free base form of 1-cyclopentylpiperazine (934 mg, 6.09 mmol), and triethylamine (0.85 mL, 6.09 mmol) in 10 mL of methylene chloride were used. It was gently refluxed at 45° C. for one over night. 1.07 g of the title compound with C-24-TBDMS group was isolated in 51% yield after silica gel chromatography. MS (FAB) m/z: M+H=1042. The obtained product (1.05 g, 1.008 mmol) was treated with 48%-HF (4 mL) in 35 mL of acetonitrile in the procedure described in Example 5 for 4 hours. After purified by reverse phase HPLC, the pure desirable title compound (459 mg) was obtained in 39% yield. MS (FAB) m/z: M+K=966. mp=124°–125° C.

EXAMPLE 32

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=cyclohexyl Following the procedure of Example 6, but replacing 1-benzylpiperazine with 1-cyclohexylpiperazine, provides the desired compound. The product of Example 3 (2.1 g, 2.03 mmol), base-treated free base form of 1-cyclohexylpiperazine (1.024 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 33

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=cycloheptyl Following the procedure of Example 6, but replacing 1-benzylpiperazine with 1-cycloheptylpiperazine, provides the desired compound. The product of Example 3 (2.1 g, 2.03 mmol), base-treated free base form of 1-cycloheptylpiperazine (1.110 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to provide the pure title compound.

EXAMPLE 34

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=cyclooctyl Following the procedures of Example 6, but replacing 1-benzylpiperazine with 1-cyclooctylpiperazine, provide the desired compound. The product of Example 3 (2.1 g, 2.03 mmol), base-treated free base form of 1-cyclooctylpiperazine (1.196 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 35

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=N-morpholinocarbonyl N-tert-butyloxycarbonylpiperazine (1.0 g, 5.34 mmol) was dissolved in 5 mL of THF:water (1:1) and cooled in an ice bath. Triethylamine (1.45 mL, 10.68 mmol), followed by 4-morpholinocarbonyl chloride (0.752 mL, 6.4 mmol) in 5 mL of ether were added, and stirred at 0° C. for 1 hour and at room temperature for 2 hours. Solvents were removed and 40 mL of ethyl acetate was added to the residue. The ethyl acetate layer was washed with brine (30 mL×3) and dried over anhydrous sodium sulfate. After filtered, the filtrate was concentrated in vacuo to yield 1.39 g of N-tert-butyloxycarbonyl-N'-morpholinocarbonyl-piperazine in 87% yield as a solid. MS m/z M+H=300, M+NH$_4$=317; H$^1$-NMR (in CDCl$_3$) δ=1.49 (s, 9H, Boc), 3.25 (m, 8H, 4×CH$_2$), 3.52 (m, 4H), 3.65 (m, 4H). The obtained N-tert-butyloxycarbonyl-N'-morpholinocarbonyl-piperazine (1.38 g, 4.62 mmol) was dissolved in 10 mL of 20% trifluoroacetic acid in methylene chloride and stirred at room temperature for 1 hour. Solvent and trifluoro acetic acid were removed to obtain N-morpholinocarbonylpiperazine trifluoroacetic acid salt in quantitative yield. MS m/z M+H=200, H$^1$-NMR (in MeOH-d$_4$) δ=3.22 (m, 4H), 3.3 (m, 4H), 3.45 (m, 4H), 3.65 (m, 4H). The obtained N-morpholinocarbonylpiperazine trifluoroacetic acid salt is dissolved in 30 mL of acetonitrile and cooled in an ice bath. Solid sodium bicarbonate is added to the acetonitrile solution and stirred for an additional 2 hours. Solid is filtered off and the filtrate is concentrated in vacuo to yield N-morpholinocarbonylpiperazine. Following the procedure of Example 6, but replacing 1-benzylpiperazine with 1-morpholinocarbonylpiperazine, provides the desired compound. The product of Example 3 (2.1 g, 2.03 mmol), 1-morpholinocarbonylpiperazine (1.212 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to yield the pure title compound.

EXAMPLE 36

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^2$=$R^{2'}$=OH Commercially available 4,4-piperidinediol hydrochloride (3.72 g, 20 mmol) is dissolved in 30 mL of acetonitrile and cooled in an ice bath. Solid sodium bicarbonate is added to the acetonitrile solution and stirred for an additional 2 hours. Solid is filtered off and the filtrate is concentrated in vacuo to yield 4,4-piperidinediol. Following the procedure of Example 6, but replacing 1-benzylpiperazine with 4,4-piperidinediol, provides the desired compound. The product of Example 3 (2.1 g, 2.03 mmol), 4,4-piperidinediol (713.4 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to yield the pure title compound.

Alternatively, the title compound is also synthesized from the compound of Example 16. Compound of Example 16 (916 mg, 1 mmol) is treated with 10 mL of cold dioxane:HCl (1:1) mixture until starting material is disappeared on TLC plate. The solution is carefully evaporated to dryness and purified by reverse phase HPLC as has been described in Example 7.

EXAMPLE 37

Formula I: $R^{100}$=H; $R^{101}$=ethyl; $R^{102}$=H; $R^{103}$=OH; $R^{104}$=H; m=1; n=1; $R^3$=$R^4$=$R^5$=H; $R^1$=methyl To a solution of homopiperazine (5 g, 50 mmol) in 10 mL of ethanol added a solution of methyl iodide (0.62 mL, 10 mmol) in 5 mL of ethanol in a sealed tube. It was gently stirred at 95° C. for 5 hours. The resulting white precipitate was filtered, washed with a small amount of cold ethanol, and the filtrate was concentrated in vacuo to yield 1-methyl homopiperazine hydroiodide. MS m/z M+H=115. The obtained 1-methylhomopiperazine hydroiodide is converted into free base according to the procedure describing in Example 25. Following the procedure of Example 6, but replacing 1-benzylpiperazine with 1-methyl homopiperazine, provides the desired compound. The product of Example 3 (2.1 g, 2.03 mmol), 1-methylhomopiperazine (700 mg, 6.09 mmol), and triethylamine (0.85 mL, 6.09 mmol) in 10 mL of methylene chloride are used. The reaction is carried out at 45° C. for 15 hours. Semi-pure compound is isolated from silica gel column chromatography. The obtained product (1.0 g, 0.9 mmol) is treated with 48%-HF (4 mL) in 30 mL of acetonitrile in the procedure described in Example 5. The pure title compound is isolated from silica gel column chromatography, followed by reverse phase HPLC.

EXAMPLE 38

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=piperonyl Following the procedure of Example 6, but replacing 1-benzylpiperazine with 1-piperonylpiperazine, provided the desired compound. The product of Example 3 (2.0 g, 1.93 mmol), 1-piperonylpiperazine (1.275 g, 5.79 mmol), and triethylamine (0.81 mL, 5.79 mmol) in 10 mL of methylene chloride were used and stirred at 45° C. for one over night. 1.2 g of pure compound was isolated after silica gel column chromatography, followed by normal phase HPLC purification in 56% yield. MS (FAB) m/z: M+H=1108. M+K=1146. The obtained product (1.2 g, 1.08 mmol) was treated with 48%-HF (4 mL) in 35 mL of acetonitrile in the procedure described in Example 5, except reaction time was 5 hours. 702 mg of the pure title compound was isolated in 53 yield after RP-HPLC purification. MS (FAB) m/z: M+H=994. M+K=1032. mp=115°–117° C.

EXAMPLE 39

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=piperonyl Following the procedure of Example 6, but replacing 1-benzylpiperazine with 1-piperazineacetophenone, provided the desired compound. The product of Example 3 (2.1 g, 2.03 mmol), 1-piperazineacetophenone (1.244 g, 6.09 mmol), and triethylamine (0.563 mL, 4.06 mmol) in 10 mL of methylene chloride were used. The reaction was carded out at 45° C. for one over night with stirring. The reaction mixture was purified on silica gel cloumn and the compound was eluted with 10% acetone in hexane to obtain semi-pure product (1.2 g). MS (FAB) m/z: M+K=1130, M+H=1092. The obtained product (2.0 g, 1.09 mmol) was treated with 48%-HF (3 mL) in 30 mL of acetonitrile and then purified in the procedure described in Example 5 to obtain the pure title compound (462 mg) in 43% yield. MS (FAB) m/z: M+K=1016. mp=116°–117° C.

EXAMPLE 40

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=4-acetylphenyl Commercially available glycerol formal (2.6 mL, 30 mmol) is treated with carbon tetrabromide (11.94 g, 36 mmol) and triphenylphosphine (11.80 g, 45 mmol) in 40 mL of methylene chloride. Fractional distilation gives the desired bromide derivative. The obtained bromo derivative is reacted with piperazine to yield its hydrobromide salt, and free base is liberated by treatment of solid sodium bicarbonate according to the method described in Example 25. Following the procedure of Example 6, but replacing 1-benzylpiperazine with the above piparazine derivative, provides the desired compound. The product of Example 3 (2.1 g, 2.03 mmol), 3-(1-piperazinyl)-1,3-dioxolanemethyl (1.049 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to yield the pure title compound.

EXAMPLE 41

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=[2,3-bishydroxy]propyl Following the procedure of Example 6, but replacing 1-benzylpiperazine with 3-(1-piperazinyl)-1,2-propanediol, provides the desired compound. The product of Example 3 (2.1 g, 2.03 mmol), 3-(1-piperazinyl)-1,2-propanediol (975.7 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 42

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-pyridylmethyl Commercially available 2-pyridylcarbinol (2.89 mL, 30 mmol) is treated with carbon tetrabromide (11.94 g, 36 mmol) and triphenylphosphine (11.80 g, 45 mmol) in 40 mL of methylene chloride to obtain 2-pyridylmethyl bromide. The obtained 2-pyridylmethyl bromide is reacted with piperazine to yield its hydrobromide salt, and free base is liberated by treatment of solid sodium bicarbonate according to the method described in Example 25. Following the procedure of Example 6, but replacing 1-benzylpiperazine with 1-[2-pyridylmethyl]piperazine, provides the desired compound. The product of Example 3 (2.1 g, 2.03 mmol), 1-[2-pyridylmethyl]piperazine (1.076 g, 6.09 mmol), and triethylamine (0.85 mL, 6.09 mmol) in 10 mL of methylene chloride are used. Pure C-24-TBDMS compound is isolated. The obtained product (1.0 g) is treated with 48%-HF (4 mL) in 35 mL of acetonitrile in the procedure described in Example 5 to yield the pure title compound.

EXAMPLE 43

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^2$ and $R^{2'}$ taken together to form —O(CH$_2$)$_i$O— wherein i=3

Following the procedure of Example 6, but replacing 1-benzylpiperazine with 4-piperidone propylene ketal, provides the desired compound. The product of Example 3 (2.1 g, 2.03 mmol), 4-piperidone propylene ketal (975.2 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 44

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^2$=N-pyrrolidino; $R^{2'}$=H Following the procedure of Example 6, but replacing 1-benzylpiperazine with 4-pyrrolidinopiperidine, provided the desired compound. The product of Example 3 (2.0 g, 1.93 mmol), 4-pyrrolidinopiperidine (891 mg, 5.79 mmol), and triethylamine (0.537 mL, 3.86 mmol) in 10 mL of methylene chloride were used. The reaction was carded out at 35° C. for 5 hours with stirring. The reaction mixture was purified on silica gel cloumn. After the by-products were eluted with 10% acetone in hexane, the compound was eluted with 5% methanol in methylene chloride to obtain semi-pure product (1.2 g) in 60% yield. MS (FAB) m/z: M+K=1080, M+H=1042. The obtained product (1.18 g, 1.13 mmol) was treated with 48%-HF (4 mL) in 35 mL of acetonitrile in the procedure described in Example 5 to obtain the pure title compound. 253 mg (24%), MS (FAB) m/z: M+K=928, M+H=966. mp=122°–125° C.

EXAMPLE 45

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^2$=N-piperidino; $R^{2'}$=H Following the procedure of Example 6, but replacing 1-benzylpiperazine with 1-piperidinopiperidine, provides the desired compound. The product of Example 3 (2.1 g, 2.03 mmol), 1-piperidinopiperidine (1.025 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 46

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^2$=N,N-dimethylamino; $R^{2'}$=H Following the procedure of Example 6, but replacing 1-benzylpiperazine with 4-dimethylaminopiperidine, provides the desired compound. The product of Example 3 (2.1 g, 2.03 mmol), 4-dimethylaminopiperidine (1.110 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 47

Formula I: $R^{100}$=H; $R^{101}$=ethyl; $R^{102}$=H; $R^{103}$=OH; $R^{104}$=H; m=0; n=1; $R^2$=$R^{2'}$=H; $R^3$=N-pyrrolidinoethyl; $R^4$=$R^5$=H Following the procedure of Example 6, but replacing 1-benzylpiperazine with 2-(2-N-pyrrolidinoethyl) piperidine, provides the desired compound. The product of Example 3 (2.1 g, 2.03 mmol), 2-(2-N-pyrrolidinoethyl) piperidine (1.110 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 48

Formula I: $R^{100}$=H; $R^{101}$=ethyl; $R^{102}$=H; $R^{103}$=OH; $R^{104}$=H; m=0; n=1; $R^2$=$R^{2'}$=H; $R^3$=N,N-dimethylaminoethyl; $R^4$=$R^5$=H Following the procedure of Example 6, but replacing 1-benzylpiperazine with 2-(2-dimethylaminoethyl) piperidine, provides the desired compound. The product of Example 3 (2.1 g, 2.03 mmol), 2-(2-dimethylaminoethyl) piperidine (951.7 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 49

Formula I: $R^{100}$=H; $R^{101}$=ethyl; $R^{102}$=H; $R^{103}$=OH; $R^{104}$=H; m=0; n=1; $R^2$=$R^{2'}$=$R^3$=(S)-N-methyl-2-piperidinomethyl; $R^4$=$R^5$=H Following the procedure of Example 6, but replacing 1-benzylpiperazine with (S)-N-methyl-2-[2'-piperidinomethyl]pyrrolidine, provides the desired compound. The product of Example 3 (2.1 g, 2.03 mmol), (S)-1-methyl-2-(2'-piperidinomethyl)pyrrolidine (1.110 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 50

Formula I: $R^{100}$=H; $R^{101}$=ethyl; $R^{102}$=H; $R^{103}$=OH; $R^{104}$=H; m=0; n=0; $R^2$=$R^{2'}$=H; $R^3$=(S)-1-[2-(pyrrolidinomethyl)]; $R^4$=$R^5$=H Following the procedure of Example 6, but replacing 1-benzylpiperazine with (S)-(+)-1-(2 -(pyrrolidinomethyl)pyrrolidine, provides the desired compound. The product of Example 3 (2.1 g, 2.03 mmol), (S)-(+)-1-(2-(pyrrolidinomethyl)pyrrolidine (939.4 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 51

Formula I: $R^{100}$=H; $R^{101}$=ethyl; $R^{102}$=H; $R^{103}$=OH; $R^{104}$=H; m=0; n=1; $R^2$=$R^{2'}$=H; $R^3$=N,N-dimethylaminomethyl; $R^4$=$R^5$=H Following the procedure of Example 6, but replacing 1-benzylpiperazine with N-(2-piperidylmethyl) dimethylamine, provides the desired compound. The product of Example 3 (2.1 g, 2.03 mmol), N-(2-piperidylmethyl) dimethylamine (866 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 52

Formula I: $R^{100}$=H; $R^{101}$=ethyl; $R^{102}$=H; $R^{103}$=OH; $R^{104}$=H; m=0; n=1; $R^2$=$R^{2'}$=H; $R^4$=N,N-diethylcarbonyl; $R^3$=$R^5$=H Following the procedure of Example 6, but replacing 1-benzylpiperazine with N,N-diethyl nipecotanide, provides the desired compound. The product of Example 3 (2.1 g, 2.03 mmol), N,N-diethyl nipecotanide (1.122 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 53

Formula I: $R^{100}$=H; $R^{101}$=ethyl; $R^{102}$=H; $R^{103}$=OH; $R^{104}$=H; m=0; n=1; $R^3$=$R^4$=$R^5$=H; X=sulfur Following the procedure of Example 6, but replacing 1-benzylpiperazine with thiomorpholine, provides the desired compound. The product of Example 3 (2.1 g, 2.03 mmol), thiomorpholine (1.122 g, 6.09 mmol), and triethylamine (612.5 μL, 6.09 mmol) in 10 mL of methylene chloride are used. The obtained product (1.0 g) is treated With 48%-HF (4 mL) in 35 mL of acetonitrile in the procedure described in Example 5 to obtain the pure title compound.

EXAMPLE 54

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=3-furoyl Following the procedure of Example 6, but replacing 1-benzylpiperazine with 1-(3-furoyl)piperazine, provides the desired compound. The product of Example 3 (2.1 g, 2.03 mmol), 1-(2-furoyl)piperazine (1.097 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 55

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=allyl Following the procedure of Example 6, but replacing 1-benzylpiperazine with 1-allylpiperazine, provides the desired compound. The product of Example 3 (2.1 g, 2.03 mmol), base-treated salt free form of 1-allylpiperazine (769 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 56

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=propargyl Following the procedure of Example 6, but replacing 1-benzylpiperazine with 1-propargylpiperazine, provides the desired compound. The product of Example 3 (2.1 g, 2.03 mmol), base-treated salt free form of 1-propargylpiperazine (756 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 57

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-pyrazinyl Following the procedure of Example 6, but replacing 1-benzylpiperazine with 1-(2-pyrazinyl)piperazine, provides the desired compound. The product of Example 3 (2.1 g, 2.03 mmol), 1-(2-pyrazinyl)piperazine (1.0 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 58

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=ethoxycarbonyl Following the procedure of Example 6, but replacing 1-benzylpiperazine with 1-ethoxycarbonylpiperazine, provided the desired compound. The product of Example 3 (2.1 g, 2.03 mmol), 1-ethoxycarbonylpiperazine (0.889 mL, 6.08 mmol), and triethylamine (0.563 mL, 4.06 mmol) in 10 mL of methylene chloride were used. The reaction was carried out at 45° C. for one over night with stirring. The reaction mixture was directly loaded on silica gel cloumn and the compound was eluted with 20% acetone in hexane to obtain semi-pure product (952 mg) in 45% yield. MS (FAB) m/z: M+K=1084, M+H=1046. The obtained product (900 mg, 0.86 mmol) was treated with 48%-HF (4 mL) in 35 mL of acetonitrile in the procedure described in Example 5 to obtain the pure title compound. 275 mg (34%), MS (FAB) m/z: M+K=970, M+H=932. mp=110°–112° C.

EXAMPLE 59

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=ethoxycarbonylmethyl Following the procedure of Example 6, but replacing 1-benzylpiperazine with N-(carboethoxymethyl)piperazine, provides the desired compound. The product of Example 3 (2.1 g, 2.03 mmol), N-(carboethoxymethyl)piperazine (1.049 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 60

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-(N,N-diethylamino)ethyl Following the procedure of Example 6, but replacing 1-benzylpiperazine with 1-[2-(diethylamino) ethyl]piperazine, provides the desired compound. The product of Example 3 (2.1 g, 2.03 mmol), base-treated salt free form of 1-[2-(dimethylamino) ethyl]piperazine (1.129 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 61

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=acetyl Following the procedure of Example 6, but replacing 1-benzylpiperazine with 1-acetylpiperazine, provided the desired compound. The product of Example 3 (2.1 g, 2.03 mmol), 1-acetylpiperazine (780.6 mg, 6.09 mmol), and triethylamine (0.563 mL, 4.06 mmol) in 10 mL of methylene chloride were used. The reaction was carried out at 45° C. for one over night with stirring. The reaction mixture was purified on silica gel cloumn. After the column was washed with 10% acetone in hexane to remove by-products, the compound was eluted with 20% acetone in hexane, followed by 2.5% methanol in methylene chloride to obtain product (0.640 g) in 31% yield. MS (FAB) m/z: M+K=1054, M+H= 1016. The obtained product (638 mg, 0.629 mmol) was treated with 48%-HF (3 mL) in 30 mL of acetonitrile and then purified in the procedure described in Example 5 to obtain the pure title compound (394 mg) in 70% yield. MS (FAB) m/z: M+K=940, M+H=902. mp=119°–120° C. (dec.).

EXAMPLE 62

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=iso-propylaminocarbonylmethyl Following the procedure of Example 6, but replacing 1-benzylpiperazine with isotroperenol, provided the desired compound. The product of Example 3 (2.0 g, 1.93 mmol), base-treated salt free form of isoproterenol (1.07 g, 5.79 mmol), and triethylamine (0.537 mL, 3.86 mmol) in 10 mL of methylene chloride were used. The reaction was carded out at 45° C. for one over night with stirring. The reaction mixture was purified on silica gel cloumn. After the column was washed with 10% acetone in hexane to remove by-products, the compound was eluted with 10% methanol in methylene chloride to obtain semi-pure product (2.1 g). MS (FAB) m/z: M+K=1111, M+H=1072. The obtained product (2.0 g, 1.86 mmol) was treated with 48%-HF (5 mL) in 40 mL of acetonitrile and then purified in the procedure described in Example 5 to obtain the pure title compound (679 mg) in 38% yield. MS (FAB) m/z: M+K=997, M+H= 959. mp=114°–118° C.

EXAMPLE 63

Formula I: $R^{100}$=H; $R^{101}$=ethyl; $R^{102}$=H; $R^{103}$=OH; $R^{104}$=H; m=0; n=1; $R^2$=$R^3$=$R^4$=$R^5$=H; $R^1$=N-methyl-N-phenylaminocarbonylmethyl Following the procedure of Example 6, but replacing 1-benzylpiperazine with piperidinoacetic acid N-methylanilide, provides the desired compound. The product of Example 3 (2.1 g, 2.03 mmol), piperidinoacetic acid N-methylanilide (1.421 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to yield the pure title compound.

EXAMPLE 64

Formula I: $R^{100}$=H; $R^{101}$=ethyl; $R^{102}$=H; $R^{103}$=OH; $R^{104}$=H; m=0; n=1; $R^2$=$R^{2'}$=$R^4$=$R^5$=H; $R^3$=N-pyrrolylmethyl Following the procedure of Example 6, but replacing 1-benzylpiperazine with 1-(2-piperidylmethyl) pyrrole, provides the desired compound. The product of Example 3 (2.1 g, 2.03 mmol), base-treated salt free form of 1-(2-piperidylmethyl) pyrrole (1.0 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 65

Formula I: $R^{100}$=H; $R^{101}$=ethyl; $R^{102}$=H; $R^{103}$=OH; $R^{104}$=H; m=0; n=1; $R^2$=$R^{2'}$=$R^3$=$R^5$=H; $R^4$=N-pyrrolyl Following the procedure of Example 6, but replacing 1-benzylpiperazine with N-[3-piperidyl]pyrrole, provides the desired compound. The product of Example 3 (2.1 g, 2.03 mmol) N-[3-piperidyl]pyrrole (915 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 66

Formula I: $R^{100}$=H; $R^{101}$=ethyl; $R^{102}$=H; $R^{103}$=OH; $R^{104}$=H; m=0; n=1; $R^2$=2-hydroxyethyl; $R^{2'}R^3$=$R^4$=$R^5$=H Following the procedure of Example 6, but replacing 1-benzylpiperazine with 4-piperidineethanol, provides the desired compound. The product of Example 3 (2.1 g, 2.03 mmol), 4-piperidineethanol (787 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 67

Formula I: $R^{100}$=H; $R^{101}$=ethyl; $R^{102}$=H; $R^{103}$=OH; $R^{104}$=H; m=0; n=1; $R^2$=hydroxy; $R^{2'}$=$R^3$=$R^4$=$R^5$=H Following the procedure of Example 6, but replacing 1-benzylpiperazine with 4-hydroxypiperidine, provided the desired compound. The product of Example 3 (2.0 g, 1.93 mmol), 4-hydroxypiperidine (0.585 ml, 5.79 mmol), and triethylamine (0.672 mL, 4.83 mmol) in 10 mL of methylene chloride were used. The obtained product (1.24 g, 65%, M+H$^+$=989) was treated with 48%-HF (4 mL) in 40 mL of acetonitrile in the procedure described in Example 5 to obtain the pure title compound (360 mg) in 33% yield. MS (FAB) m/z: M+K$^+$=913, M+H$^+$=875. mp=98°–104° C.

EXAMPLE 68

Formula I: $R^{100}$=H; $R^{101}$=ethyl; $R^{102}$=H; $R^{103}$=OH; $R^{104}$=H; m=0; n=1; $R^2$=—C(O)NH$_2$; $R^{2'}$=$R^3$=$R^4$=$R^5$=H Following the procedure of Example 6, but replacing 1-benzylpiperazine with 4-piperidine carboxamide, provides the desired compound. The product of Example 3 (2.1 g, 2.03 mmol), 4-piperidine carboxamide (780.6 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 69

Formula I: $R^{100}$=H; $R^{101}$=ethyl; $R^{102}$=H; $R^{103}$=OH; $R^{104}$=H; m=0; n=1; $R^2$=$R^{2'}$=$R^3$=$R^5$=H; $R^4$=ethoxycarbonyl Following the procedure of Example 6, but replacing 1-benzylpiperazine with ethyl nipecotate, provides the desired compound. The product of Example 3 (2.1 g, 2.03 mmol), ethyl nipecotate (957.4 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 70

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=3-chlorophenyl Following the procedure of Example 6, but replacing 1-benzylpiperazine with 1-(3-chlorophenyl) piperazine, provides the desired compound. The product of Example 3 (2.1 g, 2.03 mmol), base-treated salt free form of 1-(3-chlorophenyl)piperazine (1.198 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to yield the pure title compound.

EXAMPLE 71

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-cyanophenyl Following the procedure of Example 6, but replacing 1-benzylpiperazine with 1-(2-cyanophenyl) piperazine, provides the desired compound. The product of Example 3 (2.1 g, 2.03 mmol), 1-(2-cyanophenyl)piperazine (1.140 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to yield the pure title compound.

EXAMPLE 72

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=3,4-dimethoxyphenyl Following the procedure of Example 6, but replacing 1-benzylpiperazine with 1-(3,4-dimethoxyphenyl) piperazine, provides the desired compound. The product of Example 3 (2.1 g, 2.03 mmol), base-treated salt free form of 1-(3,4-dimethoxyphenyl)piperazine (1.353 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to yield the pure title compound.

EXAMPLE 73

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=3,4,5-trimethoxyphenyl Following the procedure of Example 6, but replacing 1-benzylpiperazine with 1-(3,4,5-trimethoxyphenyl) piperazine, provides the desired compound. The product of Example 3 (2.1 g, 2.03 mmol), base-treated salt free form of 1-(3,4,5-trimethoxyphenyl)piperazine (1.532 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to yield the pure title compound.

EXAMPLE 74

Formula I: $R^{100}$=H; $R^{101}$=ethyl; $R^{102}$=H; $R^{103}$=OH; $R^{104}$=H; m=0; n=0; $R^{2'}$=$R^3$=$R^4$=$R^5$=H; $R^2$=acetamido Following the procedure of Example 6, but replacing 1-benzylpiperazine with 3-acetamidopyrrolodine, provides the desired compound. The product of Example 3 (2.1 g, 2.03 mmol), 3-acetamidopyrrolodine (780.6 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 75

Formula I: $R^{100}$=H; $R^{101}$=ethyl; $R^{102}$=H; $R^{103}$=OH; $R^{104}$=H; m=0; n=0; $R^{2'}$=$R^3$=$R^4$=$R^5$=H; $R^2$=trifluoroacetamido Following the procedure of Example 6, but replacing 1-benzylpiperazine with 3-[trifluoroacetamido]pyrrolodine, provides the desired compound. The product of Example 3 (2.1 g, 2.03 mmol), 3-[trifluoroacetamido]pyrrolodine (1.109 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 76

Formula I: $R^{100}$=H; $R^{101}$=ethyl; $R^{102}$=H; $R^{103}$=OH; $R^{104}$=H; m=0; n=0; $R^2$=$R^{2'}$=$R^4$=$R^5$=H; $R^3$=hydroxymethyl Following the procedure of Example 6, but replacing 1-benzylpiperazine with (R)-(−)-2-pyrrolidine methanol, provided the desired compound. The product of Example 3 (2.0 g, 1.93 mmol), (R)-(=)-2-pyrrolidine methanol (0.57 1 ml, 5.79 mmol), and triethylamine (0.538 mL, 3.86 mmol) in 10 mL of methylene chloride were used. The obtained product (1.13 g, 60%, M+H$^+$=989) was treated with 48%-HF (4 mL) in 30 mL of acetonitrile in the procedure described in Example 5 to obtain the pure title compound (260 mg) in 27% yield. MS (FAB) m/z: M+K$^+$=913, M+H$^+$=875. mp=90° C. (dec.).

EXAMPLE 77

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=nitro Piperazine is carefully treated with sodium nitrite and hydrochrolic acid in aqueous media to produce N-nitopiperazine hydrochloride. The obtained N-nitopiperazine hydrochloride (2.2 g) is dissolved in 30 mL of acetonitrile and cooled in an ice bath. Solid sodium bicarbonate is added to the acetonitrile solution and stirred for 2 hours. Solid is filtered off and the filtrate is concentrated in vacuo to yield N-nitropiperazine. Following the procedure of Example 6, but replacing 1-benzylpiperazine with 1-nitropiperazine, provides the desired compound. The product of Example 3 (2.1 g, 2.03 mmol), 1-nitropiperazine (792.4 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 78

Formula I: $R^{100}$=H; $R^{101}$=ethyl; $R^{102}$=H; $R^{103}$=OH; $R^{104}$=H; m=0; n=0; $R^3$=$R^4$=$R^5$=H; X=absent Following the procedure of Example 6, but replacing 1-benzylpiperazine with azetidine, provides the desired compound. The product of Example 3 (2.1 g, 2.03 mmol), azetidine (410.6 μL, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 79

Formula I: $R^{100}$=H; $R^{101}$=ethyl; $R^{102}$=H; $R^{103}$=OH; $R^{104}$=H; m=0; n=0; $R^3$=$R^4$=$R^5$=H; X=sulfur Following the procedure of Example 6, but replacing 1-benzylpiperazine with thiazolidine, provides the desired compound. The product of Example 3 (2.1 g, 2.03 mmol), thiazolidine (480.1 μL, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 80

Formula I: $R^{100}$=H; $R^{101}$=ethyl; $R^{102}$=H; $R^{103}$=OH; $R^{104}$=H; m=0; n=0; $R^3$=$R^4$=$R^5$=H; $R^1$=N-aminocarbonylamino Following the procedure of Example 6, but replacing 1-benzylpiperazine with 1-imidazolidinyl urea, provides the desired compound. The product of Example 3 (2.1 g, 2.03 mmol), 1-imidazolidinyl urea (792.1 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 81

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-pyrimidyl The product of Example 103 (775 mg, 1 mmol) is treated with trifluoromethanesulfonic acid anhydride according to the procedure described in Example 3, and the obtained product is reacted with 1-(2-pyrimidyl)piperazine according to the method described in Example 4. The obtained crude product is purified by the method described in example 5 to yield the title compound.

EXAMPLE 82

Formula I: $R^{100}$=H; $R^{101}$=ethyl; $R^{102}$=H; $R^{103}$ taken together form a bond; $R^{104}$=H; m=0; n=1; $R^3$=$R^4$=$R^5$=H; $R^1$=2-pyrimidyl The product of Example 102 (773 mg, 1 mmol) is treated with trifluoromethanesulfonic acid anhydride according to the procedure described in Example 3, and the obtained product is reacted with 1-(2-pyrimidyl)piperazine according to the method described in Example 4. The obtained crude product is purified by the method described in example 5 to yield the title compound.

EXAMPLE 83

Formula I: $R^{100}$=H; $R^{101}$=allyl; $R^{102}$=H; $R^{103}$=OH; $R^{104}$=H; m=0; n=1; $R^3$=$R^4$=$R^5$=H; $R^1$=2-hydroxyethyl Compound [Formula I: $R^{100}$=H; $R^{101}$=allyl; $R^{102}$=H; $R^{103}$=OH; $R^{104}$=OH; $R^{105}$=H] (25.4 g, 0.0316 mol) is dissolved in a solution of imidazole (43.03 g, 0.64 mol) in dry N,N-dimethylformamide (500 mL) and tert-butyldimethylchlorosilane (47.64 g, 0.32 mol) is added in portions and stirred at room temperature for 24 hours. It is then treated in the same fashion described in Example 1 to obtain the compound [Formula I: $R^{100}$=H; $R^{101}$=allyl; $R^{102}$=H; $R^{103}$=tert-butyldimethylsilyloxy; $R^{104}$=tert-butyldimethylsilyloxy; $R^{105}$=H]. The obtained compound is treated in the same method described in Example 2 to yield the compound [Formula I: $R^{100}$=H; $R^{101}$=allyl; $R^{102}$=H; $R^{103}$=tert-butyldimethylsilyloxy; $R^{104}$=OH; $R^{105}$=H]. The product of the above reaction (4.1 g, 4.42 mmol) is dissolved in 20 mL of methylene chloride at 0° C. pyridine (3.57 mL, 44.2 mmol), followed by trifluoromethanesulfonic acid anhydride (0.74 mL, 4.42 mmol) are carefully added to the reaction mixture. It is stirred at 0° C. for 20 minutes and treated in the same procedure described in Example 3 to produce the compound [Formula I: $R^{100}$=H; $R^{101}$=allyl; $R^{102}$=H; $R^{103}$=tert-butyldimethylsilyloxy; $R^{104}$=O-trifluoromethanesulfonyl; $R^{105}$=H]. The product of the above reaction (2.2 g, 2.03 mmol) is dissolved in 10 mL of freshly distilled methylene chloride, 1-[2-hydroxyethyl]piperazine (0.7 mL, 5.7 mmol) and triethylamine (0.85 mL, 6.09 mmol) are added, and the reaction is then stirred at 50° C. for 5 hours and at room temperature for one over night. The reaction mixture is treated in the same manner described in Example 6 to produce the compound [Formula I: $R^{100}$=H; $R^{101}$=allyl; $R^{102}$=H; $R^{103}$=tert-butyldimethylsilyloxy; $R^{104}$=H; $R^{105}$=4-[2-hydroxyethyl]piperazinyl]. The product of the above reaction (962 mg, 0.94 mmol) is reacted with 48% hydrogen fluoride aqueous solution [48%-HF] by the method described in Example 5 to yield the title compound.

EXAMPLE 84

Formula I: $R^{100}$=H; $R^{101}$=allyl; $R^{102}$=H; $R^{103}$=OH; $R^{104}$=H; m=0; n=1; $R^3$=$R^4$=$R^5$=H; $R^1$=2-pyrimidyl The title compound is prepared following the procedure of Example 83, but replacing the compound [Formula I: $R^{100}$=H; $R^{101}$=allyl; $R^{102}$=H; $R^{103}$=OH; $R^{104}$=OH; $R^{105}$=H] with the compound [Formula I: $R^{100}$=H; $R^{101}$=methyl; $R^{102}$=H; $R^{103}$=OH; $R^{104}$=OH; $R^{105}$=H].

EXAMPLE 85

Formula I: $R^{100}$=H; $R^{101}$=methyl; $R^{102}$=H; $R^{103}$=OH; $R^{104}$=H; m=0; n=1; $R^3$=$R^4$=$R^5$=H; $R^1$=2-pyrimidyl The title compound is prepared following the procedure of Example 83, but replacing 1-[2-hydroxyethyl]piperazine with 1-[2-pyrimidyl]piperazine.

EXAMPLE 86

Formula I: $R^{100}$=H; $R^{101}$=n-propyl; $R^{102}$=H; $R^{103}$=OH; $R^{104}$=H; m=0; n=1; $R^3$=$R^4$=$R^5$=H; $R^1$=2-hydroxyethyl The title compound is prepared following the procedure of Example 83, but replacing the compound [Formula I: $R^{100}$=H; $R^{101}$=allyl; $R^{102}$=H; $R^{103}$=OH; $R^{104}$=OH; $R^{105}$=H] with the product of Example 104, and replacing 1-[2-hydroxyethyl]piperazine with 1-[2-hydroxyethyl]piperazinyl.

EXAMPLE 87

Formula I: $R^{100}$=H; $R^{101}$=propyl; $R^{102}$=H; $R^{103}$=OH; $R^{104}$=H; m=0; n=1; $R^3$=$R^4$=$R^5$=H; $R^1$=2-pyrimidyl The title compound is prepared following the procedure of Example 83, but replacing the compound [Formula I: $R^{100}$=H; $R^{101}$=allyl; $R^{102}$=H; $R^{103}$=OH; $R^{104}$=OH; $R^{105}$=H] with the product of Example 104.

EXAMPLE 88

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=3-chloropropyl Following the procedure of Example 6, but replacing 1-benzylpiperazine with 1-(3-chloropropyl) piperazine, provides the desired compound. The product of Example 3 (2.1 g, 2.03 mmol), 1-(3-chloropropyl) piperazine (1.158 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 89

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=pyrrolidinocarbonylmethyl Following the procedure of Example 6, but replacing 1-benzylpiperazine with 1-(pyrrolidinocarbonylmethyl)piperazine, provides the desired compound. The product of Example 3 (2.1 g, 2.03 mmol), 1-(pyrrolidinocarbonylmethyl)piperazine (1.201 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 90

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-aminoethyl 1-(2-aminoethyl)piperazine (1.29 g, 10 mmol) is dissolved in 20 mL of dioxane:water (1:1) mixture and 2-(tert-butoxycarbonyloxyimino)-2-phenylacetonitrile (2.46 g, 10 mmol) is added. The mixture is then stirred until no starting material is detected on thin layer chromatography. The obtained mixture is fractionally separated by silica gel chromatography, followed by RP-HPLC to obtain 1-[2-tert-butoxycarbonylaminoethyl]piperazine. Following the procedure of Example 6, but replacing 1-benzylpiperazine with 1-[2-tert-butoxycarbonylaminoethyl]piperazine, provides the desired compound. The product of Example 3 (2.1 g, 2.03 mmol), 1-[2-tert-butoxycarbonylaminoethyl]piperazine (1.396 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5, followed by a carefully deprotection of N-tert-butoxycarbonyl group with 10% trifluoroacetic acid to obtain the pure title compound.

EXAMPLE 91

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=N-piperazinoethyl 1,1'-ethylenedipiperazine (1.98 g, 10 mmol) is dissolved in 20 mL of dioxane:water (1:1) mixture and 2-(tert-butoxycarbonyloxyimino)-2-phenylacetonitrile (2.46 g, 10 mmol) is added. The mixture is then stirred until no starting material is detected on thin layer chromatography. The obtained mixture is fractionally separated by silica gel chromatography, followed by RP-HPLC to obtain N-[4-tert-butoxycarbonylpiperazino]ethyl-piperazine. Following the procedure of Example 6, but replacing 1-benzylpiperazine with N-[4-tert-butoxycarbonylpiperazino]ethyl-piperazine, provides the desired compound. The product of Example 3 (2.1 g, 2.03 mmol), N-[4-tert-butoxycarbonylpiperazino]ethyl-piperazine (1.817 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5, followed by a carefully deprotection of N-tert-butoxycarbonyl group with 10% trifluoroacetic acid to obtain the pure title compound.

EXAMPLE 92

Formula I: $R^{100}$=H; $R^{101}$=ethyl; $R^{102}$=H; $R^{103}$=OH; $R^{104}$=H; m=0; n=0; $R^2$=$R^{2'}$=$R^4$=$R^5$=H; $R^3$=—C(O)OH Following the procedure of Example 6, but replacing 1-benzylpiperazine with proline, provides the desired compound. The product of Example 3 (2.1 g, 2.03 mmol), proline (700 mg, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 93

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-cyclohexylethyl Following the procedure of Example 6, but replacing 1-benzylpiperazine with 1-[2-cyclohexylethyl]piperazine, provides the desired compound. The product of Example 3 (2.1 g, 2.03 mmol), 1-[2-cyclohexylethyl]piperazine (1.195 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 94

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-[3-pyridylmethylamino]-ethyl 1-(2-[3-pyridylmethylamino]-ethyl)-piperazine (2.20 g, 10 mmol) is dissolved in 20 mL of dioxane:water (1:1) mixture and 2-(tert-butoxycarbonyloxyimino)-2-phenylacetonitrile (2.46 g, 10 mmol) is added. The mixture is then stirred until no starting material is detected on thin layer chromatography. The obtained mixture is fractionally separated by silica gel chromatography, followed by RP-HPLC to obtain 1-(2-[N-tert-butoxycarbonyl-3-pyridylmethylamino]-ethyl)-piperazine. Following the procedure of Example 6, but replacing 1-benzylpiperazine with 1-(2-[N-tert-butoxycarbonyl-3 -pyridylmethylamino]-ethyl)-piperazine, provides the desired compound. The product of Example 3 (2.1 g, 2.03 mmol), 1-(2-[N-tert-butoxycarbonyl-3-pyridylmethylamino]-ethyl)-piperazine (1.951 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5, followed by a carefully deprotection of N-tert-butoxycarbonyl group with 10% trifluoroacetic acid to obtain the pure title compound.

EXAMPLE 95

Formula I: $R^{100}$=H; $R^{101}$=ethyl; $R^{102}$=H; $R^{103}$=OH; $R^{104}$=H; m=1; n=1; $R^3$=$R^4$=$R^5$=H; $R^1$=3-chloropropyl Following the procedure of Example 6, but replacing 1-benzylpiperazine with 1-(3-chloropropyl)homopiperazine, provides the desired compound. The product of Example 3 (2.1 g, 2.03 mmol), 1-(3-chloropropyl)homopiperazine (1.021 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 96

Formula I: $R^{100}$=H; $R^{101}$=ethyl; $R^{102}$=H; $R^{103}$=OH; $R^{104}$=H; m=1; n=1; $R^3$=$R^4$=$R^5$=H; $R^1$=5-iodonaphthalene-1-sulfonyl Following the procedure of Example 6, but replacing 1-benzylpiperazine with 1-(5-iodonaphthalene-1 -sulfonyl)-1H-hexahydro-1,4-diazepine, provides the desired compound. The product of Example 3 (2.1 g, 2.03 mmol), 1-(5-iodonaphthalene-1-sulfonyl)-1H-hexahydro-1,4 -diazepine (2.535 g, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 97

Formula I: $R^{100}$=H; $R^{101}$=ethyl; $R^{102}$=H; $R^{103}$=OH; $R^{104}$=H; m=2; n=1; $R^2$=$R^{2'}$$R^3$=$R^4$=$R^5$=H Following the procedure of Example 6, but replacing 1-benzylpiperazine with heptamethyleneimine, provides the desired compound. The product of Example 3 (2.1 g, 2.03 mmol), heptamethyleneimine (769 μL, 6.09 mmol), and triethylamine (0.85 mL, 6.09 mmol) in 10 mL of methylene chloride are used. The obtained product (1.0 g) is treated with 48%-HF (4 mL) in 35 mL of acetonitrile in the procedure described in Example 5 to obtain the pure title compound.

EXAMPLE 98

Formula I: $R^{100}$=H; $R^{101}$=ethyl; $R^{102}$=H; $R^{103}$=OH; $R^{104}$ and $R^{105}$ taken together form an oxo group Methylsulfide-chlorine complex was prepared by adding oxalyl chloride (0.32 g) into a stirred solution of dimethylsulfoxide (0.44 g) in methylene chloride (4 mL) and stirring at −70° C. for 0.5 hours. The solution of the complex was added in slow dropwise fashion into a stirring solution of ascomycin (1.6 g) in methylene chloride (5 mL) at −70° C. After stirring for 0.25 hours, triethylamine (1.4 g) was added at −70° C. Stirring was continued at −70° C. for 0.5 hours and then at room temperature for 1 hour. The reaction mixture was then diluted with ether (100 mL), washed with 1N HCl (aq) (2×30 mL), saturated brine (30 mL), dried over magnesium sulfate and solvent removed. The product was purified on silica gel (70 g) with ether elution. Yield: 0.95 g; MS (FAB) m/z: M+H=790.

EXAMPLE 99

Formula I: $R^{100}$=H; $R^{101}$=ethyl; $R^{102}$=H; $R^{103}$=OH; $R^{104}$=H; $R^{105}$=OH Lithium tri-t-butoxyaluminum hydride (0.2 mL, 1M in THF) was added slowly into a stirred solution of the product of Example 48 (0.056 g) in dry THF (1 mL) at −70° C. under nitrogen. After stirring at −70° C. for 3 hours, it was partitioned between ether (50 mL) and 1N HCl (10 mL). The organic phase was dried over magnesium sulfate, the solvent was removed and the product purified by prep TLC (35% acetone in hexanes). Yield: 0.025 g; MS (FAB) m/z: M+K=830.

EXAMPLE 100

Formula I: $R^{100}$=H; $R^{101}$=ethyl; $R^{102}$=H; $R^{103}$=OH; $R^{104}$=H; $R^{105}$=O-trifluoromethanesulfonyl The product of Example 99 (4.0 g, 4.42 mmol) is dissolved in 20 mL of methylene chloride at 0° C. pyridine (3.57 mL, 44.2 mmol), followed by trifluoromethanesulfonic acid anhydride (0.74 mL, 4.42 mmol) are carefully added to the reaction mixture. It is stirred at 0° C. for 20 minutes and the solvent is removed. Ethyl acetate (50 mL) is added to the residue. The organic layers are washed with brine, saturated NaHCO$_3$ (20 mL×3), brine (20 mL), 10%-NaHSO$_4$ (20 mL×3), brine (20 mL×3) and dried over anhydrous sodium sulfate. After the solvent is removed, the title compound is obtained. This compound was used for the displacement reaction without further purification and characterization.

EXAMPLE 101

Formula I: $R^{100}$=H; $R^{101}$=ethyl; $R^{102}$=H; $R^{103}$=OH; m=0; n=1; $R^3$=$R^4$=$R^5$=H; $R^1$=methyl; $R_{105}$=H The product of Example 100 (2.1 g, 2.03 mmol) is dissolved in 10 mL of freshly distilled methylene chloride, 1-methylpiperazine (1.24 mL, 10.15 mmol) and triethylamine (0.85 mL, 6.09 mmol) are added, and the reaction is then stirred at 50° C. for 5 hours and at room temperature for one over night. The reaction mixture is directly poured onto silica gel column and eluted to obtain pure title compound.

EXAMPLE 102

Formula I: $R^{100}$=H; $R^{101}$=ethyl; $R^{102}$ and $R^{103}$ taken together form a bond; $R^{104}$=OH; $R^{105}$=H Ascomycin (10 g, 12.6 mmol) and pyridinium p-toluene sulfonate (1 g, 3.98 mmol) were dissolved in 200 mL of toluene and stirred at 70° C. for one over night. Solvent was removed and the residue was purified by silica gel column chromatography, eluting with 5–10% acetone in hexane. 8.89 g of the title compound was isolated in 91% yield. MS (FAB) m/z: M+K =812.

EXAMPLE 103

Formula I: $R^{100}$=H; $R^{101}$=ethyl; $R^{102}$=H; $R^{103}$=H; $R^{104}$=OH; $R^{105}$=H The produce of Example 102 (2.2 g, 2.8 mmol) was hydrogenated in the presence of 5% rhodium on alumina (220 mg) in 100 mL of ethanol at room temperature for 1 hour. After filtered, the filtrate was concentrated in vacuo to obtain the rifle compound in quantitative yield. The obtained product was then loaded on silica gel column, and eluted with 5–10% acetone in hexane to obtain the pure title compound in 75–80 yield. MS (FAB) m/z: M+K=814.

EXAMPLE 104

Formula I: $R^{100}$=H; $R^{101}$=n-propyl; $R^{102}$=H; $R^{103}$=OH; $R^{104}$=OH; $R^{105}$=H FK-506 (150 mg, 0.2 mmol) was dissolved in 6 mL of ethyl acetate and 30 mg of 10%-palladium on charcoal was added. It was hydrogenated at room temperature for 20 minutes under one atmosphere pressure. After filtered the catalyst, the solvent was evaporated to dryness to yield 150 mg of crude product, which was then purified by silica gel column chromatography, eluting with chloroform:acetone (5:1) mixture. 114 mg of the pure title compound was isolated in 76% yield. MS (FAB) m/z: M+K=844.

EXAMPLE 105

Formula I: $R^{100}$=H; $R^{101}$=ethyl; $R^{102}$=H; $R^{103}$=OH; $R^{104}$=H; m=0; n=1; $R^2$=$R^{2'}$=$R^4$=$R^5$=H; $R^3$=hydroxymethyl Following the procedure of Example 6, but replacing 1-benzylpiperazine with (±)-2-piperidinemethanol, provided the desired compound. The product of Example 3 (2.1 g, 2.03 mmol), (±)-2-piperidinemethanol (700 mg, 6.08 mmol), and triethylamine (0.846 mL, 6.08 mmol) in 10 mL of methylene chloride were used. The reaction was carried out at 45° C. for one over night with stirring. The reaction mixture was purified on silica gel cloumn. After the column was washed with 10% acetone in hexane to remove by-products, the compound was eluted with 10% methanol in methylene chloride to obtain the product (850 mg) in 42% yield. MS (FAB) m/z: M+K=1041, M+H=1003. The obtained product (850 mg, 0.85 mmol) was treated with 48%-HF (3.5 mL) in 35 mL of acetonitrile and then purified in the procedure described in Example 5 to obtain the pure title compound (290 mg) in 39% yield. MS (FAB) m/z: M+K=927, M+H=889. mp=98°–100° C.

EXAMPLE 106

Formula I: $R^{100}$=H; $R^{101}$=ethyl; $R^{102}$=H; $R^{103}$=OH; $R^{104}$=H; m=0; n=1; $R^2$=$R^{2'}$=$R^3$=$R^5$=H; $R^4$=hydroxymethyl Following the procedure of Example 6, but replacing 1-benzylpiperazine with (±)-3-piperidinemethanol, provided the desired compound. The product of Example 3 (2.1 g, 2.03 mmol), (±)-3-piperidinemethanol (700 mg, 6.08 mmol), and triethylamine (0.846 mL, 6.08 mmol) in 10 mL of methylene chloride were used. The reaction was carried out at 45° C. for one over night with stirring. The reaction mixture was purified on silica gel cloumn. After the column was washed with 10% acetone in hexane to remove by-products, the compound was eluted with 10% methanol in methylene chloride to obtain the product (1.34 g) in 66% yield. MS (FAB) m/z: M+K=1041, M+H=1003. The obtained product (1.34 g, 1.33 mmol) was treated with 48%-HF (4 mL) in 40 mL of acetonitrile and then purified in the procedure described in Example 5 to obtain the pure title compound (247 mg) in 20% yield. MS (FAB) m/z: M+K=927, M+H=889. mp=110°–112° C.

EXAMPLE 107

Formula I: $R^{100}$=H; $R^{101}$=ethyl; $R^{102}$=H; $R^{103}$=OH; $R^{104}$=H; m=0; n=1; $R^2$=$R^{2'}$=$R^4$=$R^5$=H; $R^3$=2-hydroxyethyl Following the procedure of Example 6, but replacing 1-benzylpiperazine with (±)-2-piperidine-ethanol, provided the desired compound. The product of Example 3 (2.1 g, 2.03 mmol), (±)-3-piperidine-ethanol (785 mg, 6.08 mmol), and triethylamine (0.0.846 mL, 6.08 mmol) in 10 mL of methylene chloride were used. The reaction was carried out at 45° C. for one over night with stirring. The reaction mixture was purified on silica gel cloumn. After the column was washed with 10% acetone in hexane to remove by-products, the compound was eluted with 10% methanol in methylene chloride to obtain the product (1.32 g) in 64% yield. MS (FAB) m/z: M+H=1017. The obtained product (1.3 mg, 1.28 mmol) was treated with 48%-HF (4 mL) in 40 mL of acetonitrile and then purified in the procedure described in Example 5 to obtain the pure title compound (615mg) in 53% yield. MS (FAB) m/z: M+K=941, M+H= 903. mp=85°–90° C.

EXAMPLE 108

Formula I: $R^{100}$=H; $R^{101}$=ethyl; $R^{102}$=H; $R^{103}$=OH; $R^{104}$=H; m=0; n=1; $R^2$=$R^{2'}$=$R^3$=$R^5$=H; $R^4$=hydroxy Following the procedure of Example 6, but replacing 1-benzylpiperazine with (±)-3hydroxypiperidine, provided the desired compound. The product of Example 3 (2.0 g, 1.93 mmol), (±)-3-hydroxypiperidine(0.585 ml, 5.79 mmol), and triethylamine (0.672 mL, 4.83 mmol) in 10 mL of methylene chloride were used. The reaction was carded out at 45° C. for one over night with stirring. The reaction mixture was purified on silica gel cloumn. After the column was washed with 10% acetone in hexane to remove by-products, the compound was eluted with 10% methanol in methylene chloride to obtain the product (1.11 g) in 58% yield. MS (FAB) m/z: M+H=989. The obtained product (1.10 g, 1.113 mmol) was treated with 48%-HF (4 mL) in 40 mL of acetonitrile and then purified in the procedure described in Example 5 to obtain the pure rifle compound (149 mg) in 15% yield. MS (FAB) m/z: M+K+=913, M+H+=889.

EXAMPLE 109

Formula I: $R^{100}$=H; $R^{101}$=ethyl; $R^{102}$=H; $R^{103}$=OH; $R^{104}$=H; m=0; n=1; $R^2$=$R^{2'}$=$R^4$=$R^5$=H; $R^3$=hydroxymethyl Following the procedure of Example 6, but replacing 1-benzylpiperazine with (S)-(+)-2-pyrrolidine methanol, provided the desired compound. The product of Example 3 (2.0 g, 1.93 mmol), (S)-(+)-2-pyrrolidine methanol (0.57 1 ml, 5.79 mmol), and triethylamine (0.538 mL, 3.86 mmol) in 10 mL of methylene chloride were used. The reaction was carded out at 45° C. for one over night with stirring. The reaction mixture was purified on silica gel cloumn. After the column was washed with 10% acetone in hexane to remove by-products, the compound was eluted with 10% methanol in methylene chloride to obtain the product (1.24g) in 65% yield. MS (FAB) m/z: M+H=989. The obtained product (1.04 g, 1.06 mmol) was treated with 48%-HF (4 mL) in 40 mL of acetonitrile and then purified in the procedure described in Example 5 to obtain the pure title compound (212 mg) in 23% yield. MS (FAB) m/z: M+K+=913, M+H+=875. mp=75°–95° C.

EXAMPLE 110(a)

Formula I: $R^{100}$=H; $R^{101}$=ethyl; $R^{102}$=H; $R^{103}$=$R^{104}$=dimethylthexylsilyloxy; $R^{105}$=H Ascomycin (1 g, 1.26 mmol) was dissolved in a solution of imidazole (0.86 g, 12.6 mmol) in dry N,N-dimethylformamide (10 mL) and dimethylthexylchlorosilane (1.24 g, 6.3 mmol) was added in portions and stirred at room temperature for 3 days. Diethylether (100 ml) was added to the reaction mixture, and the organic layer was washed with saturated ammonium chloride aqueous solution (30 mL×3), 10%-NaHSO$_4$ (30 mL×3), brine (30 mL), saturated NaHCO$_3$ (30 mL×3), and brine (30 mL×3). After dired over MgSO$_4$, solvent was removed in vacuo and the solid residue was purified by silica gel chromatography (569 mg), followed by HPLC eluting with 10% acetone in hexane providing the title compound (372.5 mg) in 27% yield. MS (FAB) m/z: M+K+=1114. mp=100°–104° C.

EXAMPLE 110(b)

Formula I: $R^{100}$=H; $R^{101}$=ethyl; $R^{102}$=H; $R^{103}$=OH; $R^{104}$=dimethylthexyl-silyloxy; $R^{105}$=H During the purification of the crude product of Example 110-(a) by silica gel column chromatography, pure-mono substituted title compound (456 mg) was isolated in 39% yield MS (FAB) m/z: M+K+=972. mp=92°–94° C.

EXAMPLE 111

Formula I: $R^{100}$=H; $R^{101}$=ethyl; $R^{102}$=H; $R^{103}$=dimethylthexylsilyloxy; $R^{104}$=OH; $R_{10}$=H To a solution of 48% hydrogen fluoride aqueous solution (0.2 mL) was added Example 110(a) (0.2 g, 0.186 mmol) in acetonitrile (10 mL), and the mixture was stirred at room temperature for 30 minutes. It was cooled to 0° C. in an ice bath, and solid NaHCO$_3$ was added to the reaction mixture. It was stirred for 1 hour and solid was removed by filtration. Acetonitrile was removed, and the crude title compound was purified by silica gel column chromatography. 140 mg (81%) of pure compound was obtained. MS (FAB) m/z: M+K=972.

EXAMPLE 112

Formula I: $R^{100}$=H; $R^{101}$=ethyl; $R^{102}$=H; $R^{103}$=OH; $R^{104}$=H; m=1; n=0; $R^3$ and $R^5$ taken together=CH2; $R^1$=benzyl; $R^4$=H Following the procedure of Example 6, but replacing 1-benzylpiperazine with (1S,4S)-2-benzyl-2,5 -diazabicyclo [2.2.1]heptane, provides the desired compound. The product of Example 3 (2.0 g, 1.93 mmol), (1S,4S)-2-benzyl-2,5-diazabicyclo[2.2.1]heptane (1.09 g, 5.79 mmol), and triethylamine (0.672 mL, 4.83 mmol) in 10 mL of methylene chloride are used. The obtained product is treated with 48%-HF (4 mL) in 40 mL of acetonitrile in the procedure described in Example 5 to obtain the pure title compound.

EXAMPLE 113

Formula I: $R^{100}$=H; $R^{101}$=ethyl; $R^{102}$=H; $R^{103}$=OH; $R^{104}$=H; m=1; n=0; $R^3$ and $R^5$ taken together=CH2; $R^4$=H; X=oxygen Following the procedure of Example 6, but replacing 1-benzylpiperazine with (1S,4S)-2-oxa-5-azabicyclo[2.2.1]heptane, provides the desired compound. The product of Example 3 (2.0 g, 1.93 mmol), (1S,4S)-2-oxa-5-azabicyclo[2.2.1]heptane (587 mg, 5.79 mmol), and triethylamine (0.538 mL, 3.86 mmol) in 10 mL of methylene chloride are used. The obtained product is treated with 48%-HF (4 mL) in 30 mL of acetonitrile in the procedure described in Example 5 to obtain the pure title compound.

EXAMPLE 114

Formula I: $R^{100}$=H; $R^{101}$=ethyl; $R^{102}$=H; $R^{103}$=OH; $R^{104}$=H; m=1; n=0; $R^3$ and $R^5$=H; X=oxygen; $R^4$=N,N-dimethylaminomethyl 2-[(N,N-dimethylamino)methyl]morpholine is prepared by the method described in the literature (Araki, K. et. al., *J. Med. Chem.* 36: 1356–1363 (1993)). Following the procedure of Example 6, but replacing 1-benzylpiperazine with 2-[(N,N-dimethylamino)methyl]morpholine, provides the desired compound. The product of Example 3 (2.0 g, 1.93 mmol), 2-[(N,N-dimethylamino)methyl]morpholine (5.79 mmol), and triethylamine (0.672 mL, 4.83 mmol) in 10 mL of methylene chloride are used. The obtained product is treated with 48%-HF (4 mL) in 40 mL of acetonitrile in the procedure described in Example 5 to obtain the pure title compound.

EXAMPLE 115

Formula I: $R^{100}$=H; $R^{101}$=ethyl; $R^{102}$=H; $R^{103}$=OH; $R^{104}$=H; m=1; n=0; $R^3$ and $R^5$=H; X=oxygen; $R^4$=2-acetamidoethyl 2-(2-Acetamidoethyl)morpholine is prepared by the method described in the literature (Araki, K. et. al., *J. Med. Chem.* 36:1356–1363 (1993)). Following the procedure of Example 6, but replacing 1-benzylpiperazine with 2-(2-acetamidoethyl)morpholine, provides the desired compound. The product of Example 3 (2.0 g, 1.93 mmol), 2-(2-acetamidoethyl)morpholine (5.79 mmol), and triethylamine (0.538 mL, 3.86 mmol) in 10 mL of methylene chloride are used. The obtained product is treated with 48%-HF (4 mL) in 30 mL of acetonitrile in the procedure described in Example 5 to obtain the pure title compound.

EXAMPLE 116

Formula I: $R^{100}$=H; $R^{101}$=ethyl; $R^{102}$=H; $R^{103}$=OH; $R^{104}$=H; m=1; n=0; $R^3$ and $R^5$=H; X=oxygen; $R^4$=2-[(ethoxycarbonyl)amino]methyl 2-{[(Ethoxycarbonyl)amino]methyl}morpholine is prepared by the method described in the literature (Araki, K. et. al., *J. Med. Chem.* 36:1356–1363 (1993)). Following the procedure of Example 6, but replacing 1-benzylpiperazine with 2-{[(ethoxycarbonyl)amino]methyl}morpholine, provides the desired compound. The product of Example 3 (2.0 g, 1.93 mmol), 2-{[(ethoxycarbonyl)amino]methyl}morpholine (5.79 mmol), and triethylamine (0.672 mL, 4.83 mmol) in 10 mL of methylene chloride are used. The obtained product is treated with 48%-HF (4 mL) in 40 mL of acetonitrile in the procedure described in Example 5 to obtain the pure title compound.

EXAMPLE 117

Formula I: $R^{100}$=H; $R^{101}$=ethyl; $R^{102}$=H; $R^{103}$=OH; $R^{104}$=H; m=0; n=1; $R^3$=$R^4$=$R^5$=H; $R^1$=2-pyrimidyl The product of Example 81 (5 mmol) is dissolved in 25 mL of methylene chloride. This is added to a solution of 5 mL of methylene chloride containing tert-butyl hydroperoxide in 2,2,4-trimethylpentane (6.65 mL, 20 mmol) and selenium oxide (830 mg, 7.5 mmol). The reaction is monitored by thin layer chromatography. The mixture is stirred at room temperature until the starting material is disappeared. Solvents are removed and an approximately 100 mL of ethyl acetate is added to the residue. The ethyl acetate layer is washed with brine, dried over anhydrous sodium sulfate. Purification of the title compound is carded out by high performance liquid chromatography.

EXAMPLE 118

Formula I: $R^{100}$=F; $R^{101}$=ethyl; $R^{102}$=H; $R^{103}$=H; $R^{104}$=H; m=0; n=1; $R^3$=$R^4$=$R^5$=H; $R^1$=2-pyrimidyl A solution of the product of example 117 (100 mg) in 1 mL of methylene chloride is cooled to −78° C. in a dry ice/isopropanol bath. To this stirred solution, diethylaminosulfur trifluoride (10 μL) is added. After 3 minutes, saturated sodium bicarbonate (1 mL) is added followed by 5 mL of ethyl acetate and the mixture is warmed to room temperature. Extraction from ethyl acetate, drying over anhydrous magnesium sulfate and purification by high performance liquid chromatography gives the pure title compound.

EXAMPLE 119

Formula I: $R^{100}$=OC(O)CH$_3$; $R^{101}$=ethyl; $R^{102}$=H; $R^{103}$=H; $R^{104}$=H; m=0; n=1; $R^3$=$R^4$=$R^5$=H; $R^1$=2-pyrimidyl A solution of the product of example 117 (100 mg) in 1 mL of pyridine is cooled to 0° C. in an ice bath. To this stirred solution, N,N-dimethylaminopyridine (3 μg), followed by acetic acid anhydride (20 μl) are added. After stirred at 0° C. for 5 hours, it is stirred at room temperature for one over night. Extraction from ethyl acetate, drying over anhydrous magnesium sulfate and purification by high performance liquid chromatography gives the pure title compound.

EXAMPLE 120

In Vitro Assay of Biological Activity

The immunosuppressant activity of the compounds of the present invention was determined using the human mixed lymphocyte reaction (MLR) assay described by Kino, T. et al. in *Transplantation Proceedings* XIX (5):36–39, Suppl. 6 (1987), incorporated herein by reference. The results of the assay, shown below in Table 1, demonstrate that the compounds tested are effective immunomodulators at sub-micromolar concentrations.

TABLE 1

| Ex. # | IC$_{50}$ (M) | Ex. # | IC$_{50}$ (M) |
|---|---|---|---|
| 5 | <1 × 10$^{-6}$ | 28 | <1 × 10$^{-6}$ |
| 7 | <1 × 10$^{-6}$ | 31 | <1 × 10$^{-6}$ |
| 9 | <1 × 10$^{-6}$ | 38 | <1 × 10$^{-6}$ |
| 11 | <1 × 10$^{-6}$ | 39 | <1 × 10$^{-6}$ |
| 12 | <1 × 10$^{-6}$ | 44 | <1 × 10$^{-6}$ |
| 13 | <1 × 10$^{-6}$ | 58 | <1 × 10$^{-6}$ |
| 14 | <1 × 10$^{-6}$ | 61 | <1 × 10$^{-6}$ |
| 15 | <1 × 10$^{-6}$ | 62 | <1 × 10$^{-6}$ |
| 16 | <1 × 10$^{-6}$ | 67 | <1 × 10$^{-6}$ |
| 17 | <1 × 10$^{-6}$ | 76 | <1 × 10$^{-6}$ |
| 18 | <1 × 10$^{-6}$ | 105 | <1 × 10$^{-6}$ |
| 19 | <1 × 10$^{-6}$ | 106 | <1 × 10$^{-6}$ |
| 20 | <1 × 10$^{-6}$ | 107 | <1 × 10$^{-6}$ |
| 21 | <1 × 10$^{-6}$ | 108 | <1 × 10$^{-6}$ |
| 22 | <1 × 10$^{-6}$ | 109 | <1 × 10$^{-6}$ |
| 27 | <1 × 10$^{-6}$ | | |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound having the formula

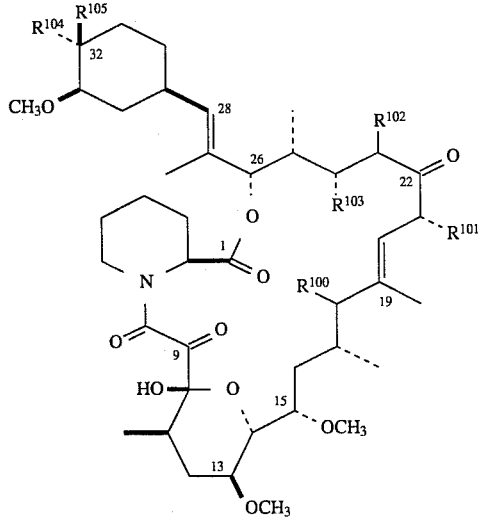

or a pharmaceutically acceptable salt, ester, amide or prodrug thereof, wherein $R^{100}$ is selected from the group consisting of hydrogen, hydroxy, halogen, —OR$^{13}$ and —OR$^{14}$;

$R^{101}$ is selected from the group consisting of methyl, ethyl, allyl and propyl;

$R^{102}$ is hydrogen and $R^{103}$ is selected from the group consisting of (a) hydrogen, (b) hydroxyl and (c) hydroxyl protected by a hydroxy-protecting group selected from tri($C_1$–$C_8$-loweralkyl)silyl, $C_1$–$C_8$-loweralkyldiarylsilyl, triarylsilyl, tri(aryl$C_1$–$C_{12}$-alkyl)silyl, triphenylmethyl-dimethylsilyl, trimethylsilylethoxycarbonyl, methylthiomethyoxyethoxycarbonyl, benzenesulfonylethoxycarbonyl, trimethylsilylethoxymethyl and aryl—C(O)— or, taken together, $R^{102}$ and $R^{103}$ form a bond; and one of $R^{104}$ and $R^{105}$ is hydrogen, and the other of $R^{104}$ and $R^{105}$ is a group having the formula

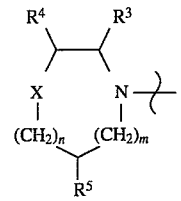

where m and n are independently zero, one or two;

X is selected from the group consisting of oxygen, —S(O)$_s$— where s is zero, one or two, —N(R$^1$)— and —C(R$^2$)(R$^2$)—, or is absent; and $R^3$, $R^4$ and $R^5$ are independently selected from the group consisting of
(a) hydrogen;
(b) $C_1$–$C_{12}$-alkyl;
(c) halo-$C_1$–$C_{12}$-alkyl;
(d) $C_3$–$C_8$-cycloalkyl;
(e) $C_3$–$C_8$-cycloalkyl-$C_1$–$C_8$alkyl;
(f) $C_2$–$C_{12}$-alkenyl;
(g) $C_2$–$C_{12}$-alkynyl;
(h) hydroxy-$C_1$–$C_8$-alkyl;
(i) hydroxyl-$C_1$–$C_8$-alkoxy-$C_1$–$C_{12}$-alkyl;
(j) aryl substituted by $R^6$, $R^7$ and $R^8$ wherein $R^6$, $R^7$ and $R^8$ are defined as below;
(j') aryl-$C_1$–$C_{12}$-alkyl substituted by $R^6$, $R^7$ and $R^8$ wherein $R^6$, $R^7$ and $R^8$ are defined as below;
(k) $C_1$–$C_8$-alkoxycarbonyl;
(l) $C_1$–$C_8$-alkoxycarbonyl-$C_1$–$C_{12}$-alkyl;
(m) carboxy-$C_1$–$C_8$-alkyl;
(n) aminoalkyl of the formula {R$^{403}$)(R$^{404}$)N-$C_1$–$C_8$-alkyl wherein $R^{403}$ and $R^{404}$ are independently selected from hydrogen, $C_1$–$C_8$-alkyl, aryl and aryl-$C_1$–$C_{12}$-alkyl or $R^{403}$ and $R^{404}$, taken together, are —(CH$_2$)$_{bb}$— wherein bb is 2–6;
(o) $C_1$–$C_{12}$-thiolalkyl;
(q) heterocyclic;
(r) (heterocyclic)-$C_1$–$C_{12}$-alkyl;
(s) (heterocyclic)-$C_1$–$C_{12}$-alkylamino-$C_1$–$C_8$-alkyl;
(u) N-mono-$C_1$–$C_{12}$-alkylamino-$C_1$–$C_8$-alkyl or N-mono-$C_3$–$C_8$-cycloalkylamino-$C_1$–$C_8$-alkyl;
(u') N,N-di-($C_1$–$C_{12}$-alkyl)amino-$C_1$–$C_8$-alkyl or N,N-di-($C_3$–$C_8$-cycloalkyl)amino-$C_1$–$C_8$-alkyl;
(v) N-mono-$C_1$–$C_{12}$-alkylcarboxamido-$C_1$–$C_8$-alkyl;
(v') N,N-di-($C_1$–$C_{12}$-alkyl)carboxamido-$C_1$–$C_8$-alkyl;
(w) N-monoarylcarboxamido-$C_1$–$C_8$-alkyl;
(w') N,N-diarylcarboxamido-$C_1$–$C_8$-alkyl;
(x) formyl;
(x') protected formyl selected from dimethylacetal, diethylacetal, bis-(2,2,2-trichloroethyl)acetal, dibenzylacetal, 1,3-dioxanyl, 5-methylene-1,3-dioxanyl, 5,5-dibromo-1,3-dioxanyl, O-methyl-S-2-[methythiol)ethyl acetal and 1,3-oxathiolanyl;
(z) (heterocyclic)-$C_2$–$C_{12}$-alkenyl; and
(aa) (heterocyclic)-$C_2$–$C_{12}$-alkynyl;

or, taken together, $R^3$ and $R^5$ form a methylene radical —CH$_2$—;

$R^1$ is selected from the group consisting of
(a) hydrogen;
(b) $C_1$–$C_{12}$-alkyl;
(c) halo-$C_1$–$C_{12}$-alkyl;

(d) $C_3$–$C_8$-cycloalkyl;
(e) $C_3$–$C_8$-cycloalkyl-$C_1$–$C_8$-alkyl;
(f) $C_2$–$C_{12}$-alkenyl;
(g) $C_2$–$C_{12}$-alkynyl;
(h) hydroxy-$C_1$–$C_8$-alkyl;
(i) hydroxyl-$C_1$–$C_8$-alkoxy-$C_1$–$C_{12}$-alkyl;
(j) aryl substituted by $R^6$, $R^7$ and $R^8$ wherein $R^6$, $R^7$ and $R^8$ are independently defined as below;
(j') aryl-$C_1$–$C_{12}$-alkyl substituted by $R^6$, $R^7$ and $R^8$ wherein $R^6$, $R^7$ and $R^8$ are independently defined as below;
(k) $C_1$–$C_8$-alkoxycarbonyl;
(l) $C_1$–$C_8$-alkoxycarbonyl-$C_1$–$C_{12}$-alkyl;
(m) carboxy-$C_1$–$C_8$-alkyl;
(n) aminoalkyl of the formula $(R^{403})(R^{404})$N-$C_1$–$C_8$-alkyl wherein $R^{403}$ and $R^{404}$ are independently defined as above;
(o) $C_1$–$C_{12}$-thiolalkyl;
(p) —S(O)$_x$—$R^9$ where x is one or two and $R^9$ is selected from the group consisting of $C_1$–$C_{12}$alkyl, aryl, and aryl-$C_1$–$C_{12}$alkyl;
(p') $C_1$–$C_{12}$-alkyl-C(O)— or aryl-C(O)—;
(q) heterocyclic;
(r) (heterocyclic)-$C_1$–$C_{12}$-alkyl;
(s) (heterocyclic)-$C_1$–$C_{12}$-alkylamino-$C_1$–$C_8$-alkyl;
(u) N-mono-$C_1$–$C_{12}$-alkylamino-$C_1$–$C_8$-alkyl or N-mono-$C_3$–$C_8$-cycloalkylamino-$C_1$–$C_8$-alkyl;
(u') N,N-di-($C_1$–$C_{12}$-alkyl)amino-$C_1$–$C_8$-alkyl or N,N-di-($C_3$–$C_8$-cycloalkyl)amino-$C_1$–$C_8$-alkyl;
(v) N-mono-$C_1$–$C_{12}$-alkylcarboxamido-$C_1$–$C_8$-alkyl;
(v') N,N-di-($C_1$–$C_{12}$-alkyl)carboxamido-$C_1$–$C_8$-alkyl;
(w) N-monoarylcarboxamido-$C_1$–$C_8$-alkyl;
(w') N, N-diarylcarboxamido-$C_1$–$C_8$-alkyl;
(x) formyl;
(x') protected formyl selected from dimethylacetal, diethylacetal, bis-(2,2,2-trichloroethyl)acetal, dibenzylacetal, 1,3-dioxanyl, 5-methylene-1,3-dioxanyl, O-methyl-S-2-(methythiol)ethyl acetal and 1,3-oxathiolanyl;
(y) —P(O)(O$R^{10}$)(O$R^{10'}$) where $R^{10}$ and $R^{10'}$ are independently selected from the group consisting of $C_1$–$C_8$-loweralkyl, aryl-$C_1$–$C_{12}$-alkyl and aryl;
(z) (heterocyclic)-$C_2$–$C_{12}$-alkenyl;
(aa) (heterocyclic)-$C_2$–$C_{12}$-alkynyl;
(bb) —NHC(O)NH$_2$;
(cc) nitro; and
(dd) polyhydroxyl-$C_1$–$C_{12}$-alkyl;

$R^2$ and $R^{2'}$ are independently selected from the group consisting of hydrogen, hydroxy, hydroxy-$C_1$–$C_8$-alkyl, $R^{402}$C(O)N($R^{401}$)-$C_1$–$C_8$-alkyl wherein $R^{401}$ and $R^{402}$ are independently selected from hydrogen $C_1$–$C_8$-alkyl, aryl, aryl-$C_1$–$C_{12}$-alkyl and halo-$C_1$–$C_{12}$-alkyl or $R^{401}$ and $R^{402}$, taken together are —(CH$_2$)$_{aa}$— wherein aa is 2–6, —C(O)NH($C_1$–$C_8$-alkyl), —C(O)N($C_1$–$C_8$-alkyl)($C_1$–$C_8$-alkyl), pyrrolidin-1-yl and piperidin-1-yl; or, taken together, $R^2$ and $R^{2'}$ are a divalent radical selected from the group consisting of oxo, thiooxo and —O(CH$_2$)$_i$O—, where i is two, three or four;

$R^6$, $R^7$ and $R^8$ are independently selected from the group consisting of
(i) hydrogen;
(ii) —($C_1$-to-$C_7$ alkyl);
(iii) —($C_2$-to-$C_6$ alkenyl);
(iv) halogen;
(v) —(CH$_2$)$_m$NR$^{11}$R$^{11'}$ where m is an integer between one and ten, and $R^{11}$ and $R^{11'}$ are independently selected from the group consisting of hydrogen, $C_1$–$C_{12}$-alkyl, aryl, aryl-$C_1$–$C_{12}$-alkyl, heterocyclic, (heterocyclic)-$C_1$–$C_{12}$-alkyl, (heterocyclic)-$C_2$–$C_{12}$-alkenyl and (heterocyclic)-$C_2$–$C_{12}$-alkynyl;
(vi) —CN;
(vii) —CHO;
(viii) mono-, di-, tri- or perhalogenated —$C_1$–$C_{12}$-alkyl;
(ix) —S(O)$_s$$R^{11}$ where s is zero, one or two and $R^{11}$ is defined as above;
(x) —C(O)NR$^{11}$R$^{11'}$ wherein $R^{11}$ and $R^{11'}$ are defined as above;
(xi) —(CH$_2$)$_m$O$R^{11}$ wherein $R^{11}$ is defined as above;
(xii) —CH(O$R^{12}$)(O$R^{12'}$), where $R^{12}$ and $R^{12'}$ are independently —($C_1$-to-$C_3$ alkyl) or, taken together, form an ethylene or propylene bridge;
(xiii) —(CH$_2$)$_m$OC(O)$R^{11}$ wherein $R^{11}$ is defined as above;
(xiv) —(CH$_2$)$_m$C(O)O$R^{11}$ wherein $R^{11}$ Is defined as above;
(xv) —O$R^{13}$, where $R^{13}$ is selected from the group consisting of
  (A) —PO(OH)OH,
  (B) —SO$_3$H, and
  (C) —C(O)(CH$_2$)$_m$C(O)OH;
(xvi) —S(O)$_t$NR$^{11}$R$^{11'}$, where t is one or two and $R^{11}$ and $R^{11'}$ are defined as above;
(xvii) —NO$_2$;
(xviii) —N$_3$; and
(xviv) guanidino optionally substituted by a radical selected from the group consisting of $C_1$–$C_8$-loweralkyl, aryl, $C_1$–$C_{12}$-alkyl-C(O)—, aryl-C(O)—, arylsulfonyl, $C_1$–$C_8$-alkoxycarbonyl, aryl-$C_1$–$C_8$-alkoxycarbonyl, aryloxycarbonyl and $C_1$–$C_{12}$-alkylsulfonyl, or any two adjacent $R^6$, $R^7$ and $R^8$ and the atoms to which they are attached form a carbocyclic or heterocyclic ring having between 5 and 7 ring atoms; and $R^{14}$ is selected from the group consisting of (i) $C_1$–$C_{12}$-alkyl-C(O)— or aryl-C(O)—; (ii) —($C_1$-to-$C_7$ alkyl); (iii) —($C_2$-to-$C_6$ alkenyl); (vi) —(CH$_2$)$_m$NR$^{11}$ R$^{11'}$, where m is an integer between one and ten and $R^{11}$ and $R^{11'}$ are independently defined as above;
(v) —S(O)$_s$$R^{11}$, where s selected from the group consisting of zero, one and two and $R^{11}$ is independently defined as above; (vi) —C(O)NR$^{11}$R$^{11'}$ wherein $R^{11}$ and $R^{11'}$ are independently defined as above; (vii) —(CH$_2$)$_m$O$R^{11}$ wherein $R^{11}$ is independently defined as above; (viii) —CH(O$R^{12}$)(O$R^{12'}$) wherein $R^{12}$ and $R^{12'}$ are independently defined as above; (ix) —(CH$_2$)$_m$OC(O)$R^{11}$ wherein $R^{11}$ is independently defined as above; (x) —(CH$_2$)$_m$C(O)O$R^{11}$ wherein $R^{11}$ is independently defined as above; and (xi) —S(O)$_t$NR$^{11}$R$^{11'}$, where t is selected from the group consisting of one and two and $R^{11}$ and $R^{11'}$ are independently defined as above:

wherein at each occurrence aryl Is independently selected from phenyl, 1-naphthyl, 2-naphthyl, fluorenyl, (1,2)-dihydronaphthyl, (1,2,3,4-)-tetrahydronaphthyl, indenyl and indanyl; and at each occurrence heterocyclic is independently selected from (i) an aromatic or non-aromatic 5-, 6- or 7-membered ring having, one, two or three heteroatoms independently selected from oxygen, sulfur and nitrogen, (ii) a bi- or tri-cyclic group comprising six-membered rings and having one, two or three heteroatoms independently selected from oxygen, sulfur and nitrogen or (iii) a 5-membered or 7-membered ring, heterocycle fused to a benzene ring; wherein in any heterocycle any of the nitrogen, sulfur and carbon atoms can be substituted with hydroxy, thiol, oxo or thioxo or any of the nitrogen atoms can be quaternized.

2. A compound according to claim 1 wherein $R^{100}$ is hydrogen.

3. A compound according to claim 1 wherein $R^{101}$ is ethyl.

4. A compound according to claim 1 wherein $R^{102}$ is hydrogen.

5. A compound according to claim 1 wherein $R^{103}$ is selected from the group consisting of hydrogen and hydroxyl.

6. A compound according to claim 1 wherein $R^{103}$ is hydroxyl protected by a hydroxy-protecting group selected from tri($C_1$–$C_8$-loweralkyl)silyl, $C_1$–$C_8$-loweralkyldiarylsilyl, triarylsilyl, tri(aryl$C_1$–$C_{12}$-alkyl)silyl, triphenylmethyldimethylsilyl, trimethylsilylethoxycarbonyl, methylthiomethyoxyethoxycarbonyl, benzenesulfonylethoxycarbonyl, trimethylsilylethoxymethyl and aryl-C(O)—.

7. A compound according to claim 1 wherein $R^{104}$ is hydrogen.

8. A compound according to claim 1 wherein m and n are integers independently selected from the group consisting of zero and one.

9. A compound according to claim 1 wherein $R^{105}$ is a radical having the formula

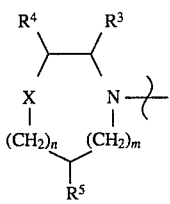

wherein X is selected from the group consisting of —S(O)$_s$—, —C($R^2$)($R^{2'}$)— and —N($R^1$)— wherein n, m, s, $R^1$, $R^2$, $R^{2'}$, $R^3$, $R^4$ and $R^5$ are as defined therein.

10. A compound according to claim 9 wherein X is selected from the group consisting of —S(O)$_s$—, —C($R^2$)($R^{2'}$) and —N($R^1$)— wherein s, $R^1$, $R^2$ and $R^{2'}$ are as defined therein.

11. A compound according to claim 9 wherein $R^1$, $R^3$, $R^4$ and $R^5$ are independently selected from the group consisting of
   (a) hydrogen;
   (b) $C_1$–$C_{12}$-alkyl;
   (c) $C_3$–$C_8$-cycloalkyl;
   (d) $C_3$–$C_8$-cycloalkyl-$C_1$–$C_8$-alkyl;
   (e) hydroxy-$C_1$–$C_8$-alkyl;
   (f) hydroxyl-$C_1$–$C_8$-alkoxy-$C_1$–$C_{12}$-alkyl;
   (g) aryl substituted by $R^6$, $R^7$ and $R^8$;
   (h) aryl-$C_1$–$C_{12}$-alkyl substituted by $R^6$, $R^7$ and $R^8$;
   (i) $C_1$–$C_8$-alkoxycarbonyl;
   (j) $C_1$–$C_8$-alkoxycarbonyl-$C_1$–$C_{12}$alkyl;
   (k) carboxy-$C_1$–$C_8$-alkyl;
   (l) aminoalkyl of the formula ($R^{403}$)($R^{404}$)N-$C_1$–$C_9$-alkyl wherein $R^{403}$ and $R^{404}$ are independently selected from hydrogen, $C_1$–$C_8$-alkyl, aryl and aryl-$C_1$–$C_{12}$-alkyl or $R^{403}$ and $R^{404}$, taken together, are —(CH$_2$)$_{bb}$— wherein bb is 2-6;;
   (m) $C_1$–$C_{12}$-thiolalkyl;
   (n) heterocyclic;
   (o) (heterocyclic)-$C_1$–$C_{12}$-alkyl;
   (p) (heterocyclic)-$C_1$–$C_{12}$-alkylamino-$C_1$–$C_8$-alkyl;
   (q) $C_1$–$C_{12}$-alkyl-C(O)— or aryl-C(O)—;
   (r) N-mono- or N,N-dialkylaminoalkyl;
   (s) N-mono- or N,N-dialkyl-carboxamidoalkyl;
   (t) N-mono- or N,N-diarylcarboxamidoalkyl; and
   (u) formyl.

12. A compound according to claim 9 wherein X is selected from the group consisting of —N($R^1$)— and —C($R^2$)($R^{2'}$)— wherein $R^2$ and $R^{2'}$ are as defined therein.

13. A compound according to claim 9 wherein the total of the integers m and n is an integer selected from the group consisting of zero, one and two.

14. A compound of the formula:

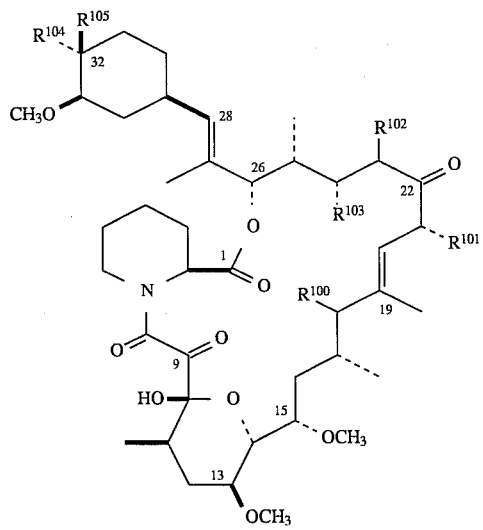

wherein one of $R^{104}$ and $R^{105}$ is hydrogen, and the other of $R^{104}$ and $R^{105}$ is a group having the formula

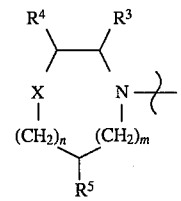

wherein
(a) $R^{100}$=H; $R^{101}$=ethyl; $R^{102}$=H; $R^{103}$=OH; $R^{104}$=H; m=0; n=1; $R^3$=$R^4$=$R^5$=H; and X is —(CH$_3$)N—;
(b) $R^{100}$=H; $R^{101}$=ethyl; $R^{102}$=H; $R^{103}$=OH; $R^{104}$=H; m=0; n=1; $R^3$=$R^4$=$R^5$=H; and X is —(benzyl)N—;
(c) $R^{100}$=H; $R^{101}$=ethyl; $R^{102}$=H; $R^{103}$=OH; $R^{104}$=H; m=0; n=1; $R^3$=$R^4$=$R^5$=H; and X is —(phenyl)N—;
(d) $R^{100}$=H; $R^{101}$=ethyl; $R^{102}$=H; $R^{103}$=OH; $R^{104}$=H; m=0; n=1; $R^3$=$R^4$=$R^5$=H; and X=—(tert-butyloxycarbonyl)N—;
(e) $R^{100}$=H; $R^{101}$=ethyl; $R^{102}$=H; $R^{103}$=OH; $R^{104}$=H; m=0; n=1; $R^3$=$R^4$=$R^5$=H; and X=—[4-nitrobenzyl]N—,
(f) $R^{100}$=H; $R^{101}$=ethyl; $R^{102}$=H; $R^{103}$=OH; $R^{104}$=H; m=0; n=1; $R^3$=$R^4$=$R^5$=H; and X=—(β-naphthylmethyl(N—,
(g) $R^{100}$=H; $R^{101}$=ethyl; $R^{102}$=H; $R^{103}$=OH; $R^{104}$=H; m=0; n=1; $R^3$=$R^4$=$R^5$=H; and X=—CH$_2$—;
(h) $R^{100}$=H; $R^{101}$=ethyl; $R^{102}$=H; $R^{103}$=OH; $R^{104}$=H; m=0; n=1; $R^3$=$R^4$=$R^5$=H; and X is —(formyl)N—;

(i) $R^{100}$=H; $R^{101}$=ethyl; $R^{102}$=H; $R^{103}$=OH; $R^{104}$=H; m=0; n=1; $R^3$=$R^4$=$R^5$=H; and X is —C($R^2$)($R^{2'}$)— wherein $R^2$ and $R^{2'}$ taken together form —O(CH$_2$)$_i$O— wherein i=2;

(j) $R^{100}$=H; $R^{101}$=ethyl; $R^{102}$=H; $R^{103}$=OH; $R^{104}$=H; m=0; n=1; $R^3$=$R^4$=$R^5$=H; and X=—(2-hydroxyethyl)N—;

(k) $R^{100}$=H; $R^{101}$=ethyl; $R^{102}$=H; $R^{103}$=OH; $R^{104}$=H; m=0; n=1; $R^3$=$R^4$=$R^5$=H; and X=oxygen;

(l) $R^{100}$=H; $R^{101}$=ethyl; $R^{102}$=H; $R^{103}$=OH; $R^{104}$=H; m=0; n=1; $R^3$=$R^4$=$R^5$=H; and X=—(2-(2-hydroxyethoxy)ethyl)N—;

(m) $R^{100}$=H; $R^{101}$=ethyl; $R^{102}$=H; $R^{103}$=OH; $R^{104}$=H; m=0; n=1; $R^3$=$R^4$=$R^5$=H; and X=—(2-pyridyl)N—

(n) $R^{100}$=H; $R^{101}$=ethyl; $R^{102}$=H; $R^{103}$=OH; $R^{104}$=H; m=0; n=1; $R^3$=$R^4$=$R^5$=H; and X=—(2-pyrimidyl)N—;

(o) $R^{100}$=H; $R^{101}$=ethyl; $R^{102}$=H; $R^{103}$=OH; $R^{104}$=H; m=0; n=1; $R^3$=$R^4$=$R^5$=H; and X=—NH—;

(p) $R^{100}$=H; $R^{101}$=ethyl; $R^{102}$=H; $R^{103}$=OH; $R^{104}$=H; m=0; n=1; $R^3$=$R^4$=$R^5$=H; and X=1-(—pyrrolidinocarbonylmethyl)N—;

(q) $R^{100}$=H; $R^{101}$=ethyl; $R^{102}$=H; $R^{103}$=OH; $R^{104}$=H; m=0; n=1; $R^3$=$R^4$=$R^5$=H; and X=—(1-morpholinocarbonylmethyl)N—;

(r) $R^{100}$=H; $R^{101}$=ethyl; $R^{102}$=H; $R^{103}$=OH; $R^{104}$=H; m=0; n=1; $R^3$=$R^4$=$R^5$=H; and X is —(cyclopentyl)N—;

(s) $R^{100}$=H; $R^{101}$=ethyl; $R^{102}$=H; $R^{103}$=OH; $R^{104}$=H; m=0; n=1; $R^3$=$R^4$=$R^5$=H; and X=—(piperonyl)N—, (t) $R^{100}$=H; $R^{101}$=ethyl; $R^{102}$=H; $R^{103}$=OH; $R^{104}$=H; m=0; n=1; $R^3$=$R^4$=$R^5$=H; and X=—(4-acetylphenyl)N—;

(u) $R^{100}$=H; $R^{101}$=ethyl; $R^{102}$=H; $R^{103}$=OH; $R^{104}$=H; m=0; n=1; $R^3$=$R^4$=$R^5$=H; and X is —C($R^2$)($R^{2'}$)— wherein $R^2$=N-pyrrolino and $R^{2'}$=H;

(v) $R^{100}$=H; $R^{101}$=ethyl; $R^{102}$=H; $R^{103}$=OH; $R^{104}$=H; m=0; n=1; $R^3$=$R^4$=$R^5$=H; and X=—(ethoxycarbonyl)N—;

(w) $R^{100}$=H; $R^{101}$=ethyl; $R^{102}$=H; $R^{103}$=OH; $R^{104}$=H; m=0; n=1; $R^3$=$R^4$=$R^5$=H; and X=—(acetyl)N—;

(x) $R^{100}$=H; $R^{101}$=ethyl; $R^{102}$=H; $R^{103}$=OH; $R^{104}$=H; m=0; n=1; $R^3$=$R^4$=$R^5$=H; and X=—(iso-propylaminocarbonylmethyl)N—;

(y) $R^{100}$=H; $R^{101}$=ethyl; $R^{102}$=H; $R^{103}$=OH; $R^{104}$=H; m=0; n=1; $R^3$=$R^4$=$R^5$=H; and X is —C($R^2$)($R^{2'}$)— wherein $R^2$=hydroxy and $R^{2'}$=H;

(z) $R^{100}$=H; $R^{101}$=ethyl; $R^{102}$=H; $R^{103}$=OH; $R^{104}$=H; m=0; n=0; $R^4$=$R^5$=H; $R^3$=hydroxymethyl; and X is —CH$_2$—;

(aa) $R^{100}$=H; $R^{101}$=ethyl; $R^{102}$=H; $R^{103}$=OH; $R^{104}$=H; m=0; n=1; $R^4$=$R^5$=H; $R^3$=hydroxymethyl; and X is —CH$_2$—;

(bb) $R^{100}$=H; $R^{101}$=ethyl; $R^{102}$=H; $R^{103}$=OH; $R^{104}$=H; m=0; n=1; $R^4$=$R^5$=H; $R^4$=hydroxymethyl; and X is —CH$_2$—;

(cc) $R^{100}$=H; $R^{101}$=ethyl; $R^{102}$=H; $R^{103}$=OH; $R^{104}$=H; m=0; n=1; $R^4$=$R^5$=H; $R^3$=2-hydroxyethyl; and X is —CH$_2$—;

(dd) $R^{100}$=H; $R^{101}$=ethyl; $R^{102}$=H; $R^{103}$=OH; $R^{104}$=H; m=0; n=1; $R^3$=$R^5$=H; $R^4$=hydroxy; and X is —CH$_2$—; or (ee) $R^{100}$=H; $R^{101}$=ethyl; $R^{102}$=H; $R^{103}$=OH; $R^{104}$=H; m=0; n=1; $R^4$=$R^5$=H; $R^3$=hydroxymethyl; and X is —CH$_2$—;

or a pharmaceutically acceptable salt, ester, amide or prodrug thereof.

15. A compound of the formula:

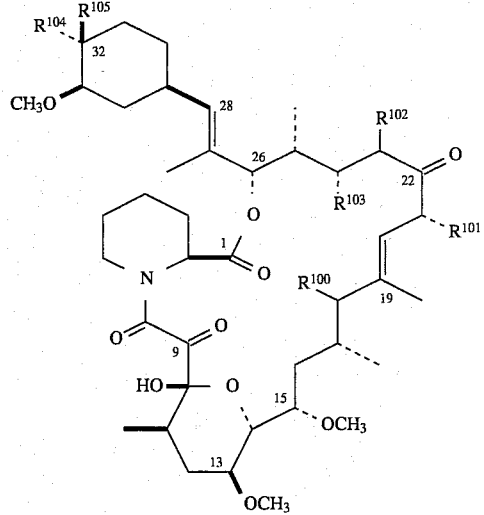

wherein (a) $R^{100}$=H; $R^{101}$=ethyl; $R^{102}$=H; $R^{103}$=$R^{104}$=dimethylthexylsilyloxy; and $R^{105}$=H;

(b) $R^{100}$=H; $R^{101}$=ethyl; $R^{102}$=H; $R^{103}$=OH; $R^{104}$=dimethylthexyl-silyloxy; and $R^{105}$=H; or $R^{100}$=H; $R^{101}$=ethyl; $R^{102}$=H; $R^{103}$=dimethylthexylsilyloxy; $R^{104}$=OH; $R_{10}$=H.

16. A compound of the formula:

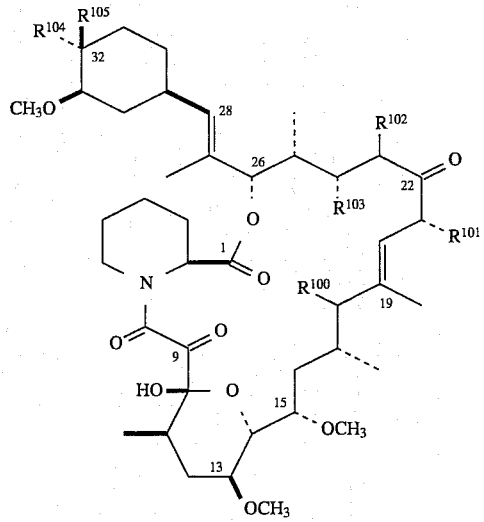

wherein one of $R^{104}$ and $R^{105}$ is hydrogen, and the other of $R^{104}$ and $R^{105}$ is a group having the formula

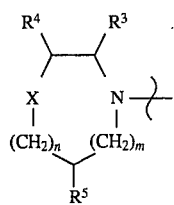
wherein $R^{100}$=H; $R^{101}$=ethyl; $R^{102}$=H; $R^{103}$=OH; $R^{104}$=H; m=0; n=1; $R^3$=$R^4$=$R^5$=H; and X=—(acetyl)N—;
or a pharmaceutically acceptable salt, ester, amide or prodrug thereof.
* * * * *

UNITED STATES PATENT AND TRADEMARK OFFICE
CERTIFICATE OF CORRECTION

PATENT NO. : 5,530,119
DATED : June 25, 1996
INVENTOR(S) : M. Kawai, et. Al.

It is certified that error appears in the above-indentified patent and that said Letters Patent is hereby corrected as shown below:

Column 54, between lines 42 and 43, insert --(p) $C_1$-$C_{12}$-alkyl-C(O)-or aryl-C(O)-;--.

Column 54, lines 58-59, change "[methythiol)" to --(methythiol)--.

Column 55, lines 38-39, change "O-methyl-S-2-(methythiol)ethyl acetal and 1,3-oxathiolanyl;" to --5,5-dibromo-1,3-dioxanyl, O-methyl-S-2-(methythiol)ethyl acetal and 1,3-oxathiolanyl--.

Column 56, line 18, change "Is" to --is--.

Column 57, line 34, change "Is" to --is--.

UNITED STATES PATENT AND TRADEMARK OFFICE
CERTIFICATE OF CORRECTION

PATENT NO. : 5,530,119

DATED : June 25, 1996

INVENTOR(S) : M. Kawai, et al

It is certified that error appears in the above-indentified patent and that said Letters Patent is hereby corrected as shown below:

Column 57, line 56, change "$C_1$-$C_9$" to --$C_1$-$C_8$--.

Column 58, lines 61-62, change "(β-naphthylmethyl(N-" to --(β-naphthylmethyl)N- --.

Column 59, line 60, change "$R^4$=$R^5$=H" to --$R^3$=$R^5$=H--.

Column 60, line 39, change "$R^{100}$=H" to --(c) $R^{100}$=H--.

Signed and Sealed this

Seventh Day of January, 1997

*Attest:*

BRUCE LEHMAN

*Attesting Officer*      *Commissioner of Patents and Trademarks*